(12) United States Patent
Tubishevitz et al.

(10) Patent No.: US 10,182,908 B2
(45) Date of Patent: Jan. 22, 2019

(54) INTRACARDIAC DEVICES COMPRISING STABILIZING ELEMENTS HAVING IMPROVED FATIGUE RESISTANCE

(71) Applicant: MVALVE TECHNOLOGIES LTD., Herzliya (IL)

(72) Inventors: Amit Tubishevitz, Tel Aviv (IL); Shay Dubi, Tel Aviv (IL); Vadim Bernshtein, Haifa (IL); Maurice Buchbinder, La Jolla, CA (US)

(73) Assignee: MVALVE TECHNOLOGIES LTD., Herzliya (IL)

( * ) Notice: Subject to any disclaimer, the term of this patent is extended or adjusted under 35 U.S.C. 154(b) by 0 days.

(21) Appl. No.: 15/100,020

(22) PCT Filed: Nov. 27, 2014

(86) PCT No.: PCT/IL2014/051030
§ 371 (c)(1),
(2) Date: May 27, 2016

(87) PCT Pub. No.: WO2015/079443
PCT Pub. Date: Jun. 4, 2015

(65) Prior Publication Data
US 2017/0252154 A1   Sep. 7, 2017

Related U.S. Application Data

(60) Provisional application No. 61/910,064, filed on Nov. 28, 2013, provisional application No. 61/910,066, (Continued)

(51) Int. Cl.
*A61F 2/24*   (2006.01)

(52) U.S. Cl.
CPC .... *A61F 2/2418* (2013.01); *A61F 2220/0008* (2013.01); *A61F 2250/0036* (2013.01); *A61F 2250/0063* (2013.01)

(58) Field of Classification Search
CPC ......... A61F 2/24; A61F 2/2445; A61F 2/2418
(Continued)

(56) References Cited

U.S. PATENT DOCUMENTS 8,029,518 B2 * 10/2011 Goldfarb .......... A61B 17/00234
606/139
8,858,623 B2 * 10/2014 Miller ................... A61F 2/2445
623/2.36

(Continued)

FOREIGN PATENT DOCUMENTS

CN         101489492         7/2009
WO    WO 2012/031141        3/2012
(Continued)

OTHER PUBLICATIONS

International Search Report for PCT/IL2014/051030, dated Feb. 26, 2015, 4 pages.
(Continued)

*Primary Examiner* — Suzette J Gherbi
(74) *Attorney, Agent, or Firm* — Nixon & Vanderhye P.C.

(57) ABSTRACT

The present invention provides an intracardiac device suitable for minimally-invasive delivery, wherein said device comprises a device body and one more stabilizing elements attached to said device body. The stabilizing elements may be selected from the group consisting of: stabilizing wings having at least one portion with a thickness greater than that of the device body, wings comprising one or more auxiliary support arms, wings having a metal wire coil wound around them, wings having a leaf spring attached thereto, polymer-coated stabilizing wings, and mechanical stabilization elements comprising a rotatable jaw-like structure.

7 Claims, 26 Drawing Sheets

Related U.S. Application Data filed on Nov. 28, 2013, provisional application No. 61/915,020, filed on Dec. 12, 2013, provisional application No. 62/066,929, filed on Oct. 22, 2014.

(58) Field of Classification Search
USPC .............................. 623/2.1–2.19, 2.36–2.38
See application file for complete search history.

(56) References Cited

U.S. PATENT DOCUMENTS

| | | | |
|---|---|---|---|
| 9,610,161 B2* | 4/2017 | Macoviak | A61F 2/2445 |
| 9,730,792 B2* | 8/2017 | Lutter | A61F 2/2418 |
| 2006/0229708 A1* | 10/2006 | Powell | A61B 17/00234 |
| | | | 623/1.24 |
| 2011/0060407 A1* | 3/2011 | Ketai | A61B 17/00234 |
| | | | 623/2.37 |
| 2012/0078360 A1 | 3/2012 | Rafiee | |
| 2013/0035759 A1* | 2/2013 | Gross | A61F 2/2439 |
| | | | 623/2.38 |
| 2013/0310928 A1* | 11/2013 | Morriss | A61F 2/2418 |
| | | | 623/2.12 |
| 2014/0324164 A1* | 10/2014 | Gross | A61F 2/2409 |
| | | | 623/2.37 |
| 2015/0094802 A1* | 4/2015 | Buchbinder | A61F 2/2454 |
| | | | 623/2.18 |
| 2015/0119981 A1* | 4/2015 | Khairkhahan | A61F 2/2442 |
| | | | 623/2.36 |
| 2016/0030169 A1* | 2/2016 | Shahriari | A61F 2/2409 |
| | | | 623/2.18 |
| 2016/0158003 A1* | 6/2016 | Wallace | A61F 2/2409 |
| | | | 623/2.17 |
| 2016/0166382 A1* | 6/2016 | Nguyen | A61F 2/2454 |
| | | | 623/2.17 |
| 2017/0100245 A1* | 4/2017 | Subramanian | A61F 2/2436 |

FOREIGN PATENT DOCUMENTS

| | | |
|---|---|---|
| WO | WO 2012/095159 | 7/2012 |
| WO | WO 2013/021375 | 2/2013 |
| WO | WO 2013/128436 | 9/2013 |
| WO | WO 2013/150512 | 10/2013 |
| WO | WO 2014/111918 | 7/2014 |

OTHER PUBLICATIONS

Written Opinion of the ISA for PCT/IL2014/051030, dated Feb. 26, 2015, 5 pages.

* cited by examiner

*Fig.* 4

Starting Position

Stage 1 position

Stage 2 position

INTRACARDIAC DEVICES COMPRISING STABILIZING ELEMENTS HAVING IMPROVED FATIGUE RESISTANCE

This application is the U.S. national phase of International Application No. PCT/IL2014/051030 filed 27 Nov. 2014, which designated the U.S. and claims priority to US Provisional Application Nos. 61/910,064 filed 28 Nov. 2013, 61/910,066 filed 28 Nov. 2013, 61/915,020 filed 12 Dec. 2013, and 62/066,929 filed 22 Oct. 2014, the entire contents of each of which are hereby incorporated by reference.

FIELD OF THE INVENTION

The present invention relates to stabilizing elements that are suitable for anchoring intracardiac devices within their intended deployment site in the heart. In particular, the stabilizing elements of the present invention are characterized in having significantly greater fatigue-resistance than those previously developed.

BACKGROUND OF THE INVENTION

In recent years, many different intracardiac devices aimed at either repairing or replacing dysfunctional mitral valves have been developed. Examples of these include various cardiac valve support devices, the purpose of which is to provide a stable 'landing pad' for subsequently implanted prosthetic valves. Examples of such support devices may be in found in co-owned, co-pending WO 2012/031141 which discloses and teaches two-ring devices, as well as in WO 2013/128436 which relates to single-ring valve support devices. Both of these publications also teach two-stage methods for replacement heart valve implantation, wherein the first stage comprises the stable implantation of a support device, while the second stage comprises the delivery and implantation of a replacement valve within the central lumen of said support device.

One technical problem encountered in the use of all such devices is the need for said devices to remain in their intended position within or near to the mitral annulus, despite the fact that the contracting heart exerts displacing pressures in the order of 200 mmHg thereon. When the size of a typical stabilizing element is taken into account, said elements are subjected to forces of approximately 16 N. The design of adequate stabilizing (where "stabilization" refers to stabilization and/or anchoring and/or attaching to the heart) elements is further complicated by the fact that the operating environment of a device implanted within the mitral annulus is such that the displacing forces are not constant, but rather they are cyclical in nature. Consequently, said stabilizing and anchoring elements must be capable of withstanding high level stress forces, the magnitude of which changes rapidly, over both the short term (immediately after implantation) and over the long term (weeks, months and years) without succumbing to low and high cycle fatigue and subsequent crack formation and development to fracture.

While the list of possible stabilization strategies is—in theory—very long, there are various operative constraints that limit the selection of stabilizing means that may be used in practice. One such constraint is a limit on the dimensions of the stabilizing wings or arms that may be formed as part of the device, or attached thereto, in view of the fact that in most cases, it is highly desirable to deliver the intracardiac device to its working location in a minimally-invasive manner, such as by a transcatheter approach (for example, trans-apical, transseptal, transfemoral approaches). Such an approach requires that the device—including the stabilizing elements—be folded or 'crimped' to as small a crossing profile as possible, in order to facilitate packing within a delivery catheter that is itself small enough to pass through various blood vessels on its way to the deployment site at the mitral (or other cardiac) annulus.

Many prior art attempts at stabilizing crimpable mitral repair and/or replacement devices have been unsuccessful as a consequence of the contradictory requirements of a) a small crossing profile of the device, and b) sufficient robustness (i.e. size and material strength) of the device, in order to withstand displacing and fatigue-inducing forces, following deployment.

A pressing need therefore exists for new elements and strategies for the effective, long-term stabilization of devices such as replacement valves and their support structures at the mitral annulus, without interfering with the ability to crimp said devices to a size that is small enough to permit their packing into appropriately-sized catheters.

The present inventors have now developed new stabilizing and attachment element designs that meet this need.

SUMMARY OF THE INVENTION

The present invention is primarily directed to an intracardiac device suitable for minimally-invasive delivery, wherein said device comprises a device body and one or more fatigue-resisting stabilizing elements attached to said device body, wherein said stabilizing elements are selected from the group consisting of:
  a) stabilizing wings having at least one portion with a thickness greater than that of the device body;
  b) stabilizing wings comprising one or more primary anchoring arms, which are capable of applying upwards axially-directed stabilizing forces onto the cardiac tissue following implantation, and one or more support arms;
  c) stabilizing wings having a metal wire coil wound therearound;
  d) stabilizing wings having a leaf spring attached thereto;
  e) polymer-coated stabilizing wings;
  f) mechanical stabilization elements comprising a rotatable jaw-like structure.

In the various embodiments and implementations of the present invention, the intracardiac device may be any device that is intended for implantation within the heart, including (but not limited to) replacement heart valves, support devices for replacement heart valves, annuloplasty rings and other devices used for repair or replacement of anatomical cardiac valves.

In one preferred embodiment, the intracardiac device is a generally annular, or ring-shaped, device characterized in having an inner circumference and an outer circumference. In one particularly preferred embodiment the ring-shaped intracardiac device is a valve support device. Most particularly, the intracardiac device is a valve support device suitable in size and form for implantation within the mitral valve annulus. In these embodiments, the body of the device consists of the generally ring-shaped portion, to which the stabilizing elements are appended (either by means of being separately attached thereto, or by means of being manufactured in one piece therewith).

In many preferred embodiments, the intracardiac device may comprise two or more stabilizing elements of the same type. In some particularly preferred embodiments, the device is fitted with two stabilizing elements of the same type (e.g. two polymer-coated stabilizing wings or two mechanical stabilization elements). In many such cases, the two stabilizing elements are arranged around the circumference of the ring shaped intracardiac device, such that they may be aligned along the two ends of the commissural line. In this way, said stabilizing elements will not interfere with the functioning of the native valve leaflets. This arrangement is particularly important in cases in which the intracardiac device is a valve support device used in a two-stage implantation procedure, such as described in co-owned, co-pending patent applications WO 2012/031141 and WO 2013/128436, in which the native valve continues to function after implantation of the valve support device, prior to the subsequent implantation of a prosthetic device. In such cases, the stabilizing elements may be arranged around the circumference of the ring-shaped intracardiac device such that they are separated by approximately 180 degrees (for example, 180 degrees, +/−20 degrees). In other embodiments, however, other spatial arrangements and more than two stabilizing elements are also possible.

In some preferred embodiments, the intracardiac device may be fitted with two or more stabilizing elements selected from two or more of the above-defined groups of embodiments. Thus, for example, in one embodiment, the intracardiac device may comprise one or more stabilizing wings, each of which are fitted both with a polymer coating and with a leaf spring. In another example, the intracardiac device may comprise one or more polymer coated stabilizing wings and, in addition, one or more mechanical stabilizing elements. All other possible combinations of the above-defined groups of stabilizing elements also fall within the scope of the present invention.

In one aspect, the present invention is directed to an intracardiac device as defined hereinabove, wherein said device comprises one or more stabilizing or anchoring wings having at least one portion with a thickness greater than that of the device body.

In one preferred embodiment of this aspect, each stabilizing wing has, along its entire length and width, a uniform thickness that is greater than the thickness of the body of the device. In another preferred embodiment, the thickness of the wing varies at different points along its length, at least one region of said wing being thicker than the thickness of the device body.

In another aspect, the present invention is directed to an intracardiac device as defined hereinabove, wherein said device comprises one or more stabilizing wings, wherein each of said wings comprises one or more primary anchoring arms, which are capable of applying upwards axially-directed stabilizing forces, and one or more support arms. The term "anchoring arm" is used to refer to the portion of the stabilizing wing which comes into contact with, and applies stabilizing forces on, the cardiac tissue. The term "support arm" is used to refer to an auxiliary arm (i.e. an arm or wing in addition to the anchoring arm), the purpose of which is to reduce the total stress and strain exerted by the contracting heart on the aforementioned primary stabilizing arm. In one preferred embodiment, the primary support arm passes medially and either axially upwards or axially downwards (wherein the term "axially" refers to the longitudinal axis of the intracardiac device, which following implantation is coaxial with the longitudinal axis of the heart).

In one preferred embodiment of this aspect of the invention, the stabilizing wing defined in the previous paragraph further comprises a connecting arm that is oriented essentially vertically downwards with respect to the device body, having a distal extremity ending at a first branch point, and a proximal end continuous with the device body, and wherein said stabilizing wing distal to said first branch point comprises (a) one or more primary anchoring arms, each having a distal end above and lateral to the outer surface perimeter of the device body, and (b) one or more primary support arms, each of which passes medially and generally either axially upwards or axially downwards from its point of origin at said first branch point.

It is to be noted that the terms "proximal" and "distal", when used in relation to the stabilization elements (wings, arms and portions thereof) refer to the ends closest to their attachment to the intracardiac device body, and further from said attachment, respectively.

In a further preferred embodiment of this aspect of the invention, the stabilizing wing further comprises a secondary support arm having a proximal end that is continuous with the connecting arm or the primary stabilizing arm or the primary support arm, and a distal arm that passes in a medial direction.

As explained hereinabove, the various main groups of stabilizing elements may be combined within one device. Thus, in one preferred embodiment of the device of the present invention, one or more of the connecting arm(s), the primary support arm(s) and the secondary support arm(s) are covered with a polymeric sleeve.

In another aspect, the present invention is directed to an intracardiac device as defined hereinabove, wherein said device comprises one or more stabilizing elements attached to the device body, and wherein said stabilizing elements are selected from the group consisting of:
a) stabilizing wings having a wire coil wound therearound;
b) stabilizing wings having one or more leaf springs attached thereto;
c) polymer-coated stabilizing wings.

In one preferred embodiment of this aspect of the invention, the stabilizing elements comprise stabilizing wings having a wire coil wound therearound, wherein said coil may be wound around either the entire length of each wing or only a portion thereof.

In another preferred embodiment of this aspect of the invention, the stabilizing elements comprise stabilizing wings having a leaf spring attached thereto, wherein said spring may be attached by either one or by both of its ends to either the inner curvature or the outer curvature of the stabilizing wing.

In a particularly preferred embodiment of this aspect of the invention, the stabilizing elements comprises stabilizing wings that are coated—either along their entire length or only along a portion thereof—with a polymer such as (but not limited to) silicone, Polytetrafluoroethylene PTFE and polyethylene (PE).

In a further aspect, the present invention is directed to an intracardiac device as defined hereinabove, wherein said device comprises one or more mechanical stabilization elements, each of said elements comprising a jaw-like structure, wherein said jaw-like structure comprises a fixed arm and a movable arm, said movable arm being pivotable in relation to said fixed arm around a common pivot point, and wherein said mechanism further comprises mechanical rotation means for causing said movable arm to rotate around said pivot point, thereby causing either closure or opening of said jaw-like structure.

In one preferred embodiment of this aspect of the invention, the aforementioned mechanical rotation means comprise a spring which is biased such that it causes closure of the jaw-like structure, a release mechanism for said spring and a ratchet mechanism for preventing accidental reverse rotation of said jaw-like structure. In one preferred implementation, said spring release mechanism comprises a control wire.

In another preferred embodiment of this aspect of the invention, the aforementioned mechanical rotation means comprise a worm gear actuated by a torque wire.

In yet another preferred embodiment of this aspect of the invention, the aforementioned mechanical rotation means comprise a threaded rod passing through a threaded aperture that pierces the movable arm.

As described hereinabove, the intracardiac device of the present invention may be any suitable type of device that is capable of being implanted within the heart. In particularly preferred embodiments however, said device is selected from the group consisting of single-ring valve support device, two-ring valve support device and prosthetic cardiac valve. In a particularly preferred embodiment, the intracardiac device of the present invention, comprising one or more of the fatigue-resisting stabilizing elements defined hereinabove is a single-ring valve support device suitable for minimally-invasive implantation within the mitral valve annulus.

It is to be noted that the terms "stabilizing", "stabilization" and "anchoring" are used interchangeably throughout this disclosure. Similarly, the terms "stabilizing wing", "stabilizing arm" and "stabilizing element" (and variants thereof) have the same meaning as each other and may be used interchangeably. Generally, the stabilizing wings of the present invention are curved, and therefore possess both outer and inner curvatures.

DETAILED DESCRIPTION OF PREFERRED EMBODIMENTS OF THE INVENTION

First Main Embodiment

Figure 1:
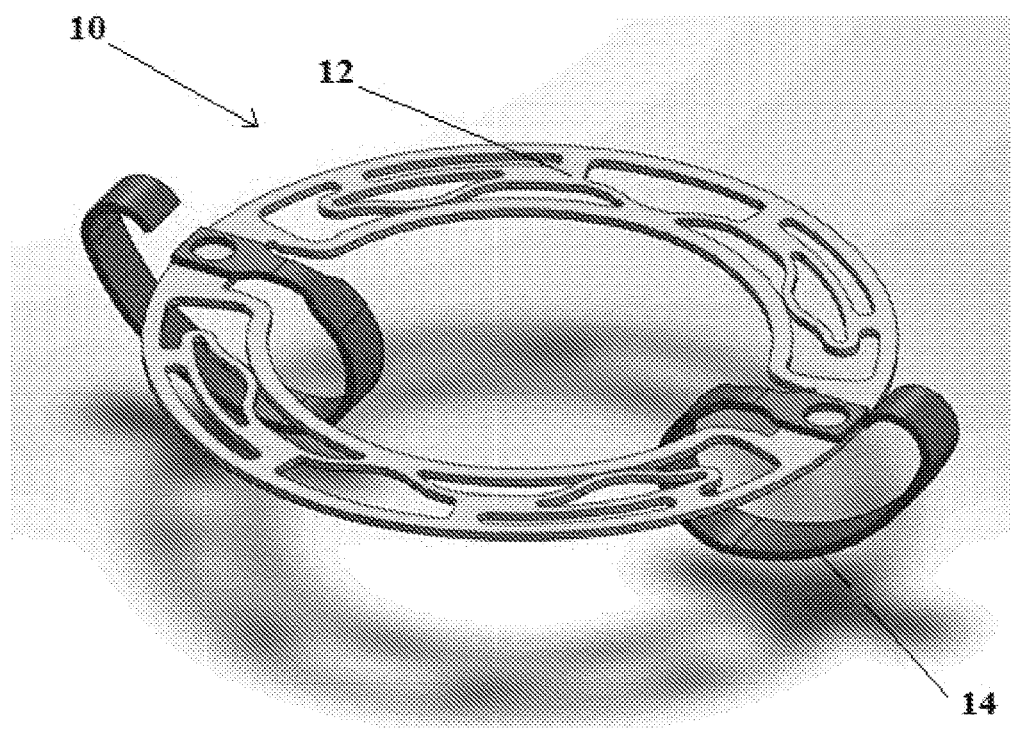
FIG. 1 illustrates a single-ring valve support of the prior art comprising two anchoring wings.

The present inventors have now found that it is possible to manufacture an intracardiac device in which different regions of said device have different thicknesses. In this way, it is possible to construct a device in which at least a portion of the one or more stabilizing wings is thicker than the body of the device. It has been found by the present inventors that this modification enables the manufacture of an intracardiac device that has greater resistance to displacement following deployment in the heart, as well as a greater resistance to fatigue and fracture, but which does not lead to an increased crossing profile of the crimped device.

This approach is, in fact, counter-intuitive, since all of the standard manufacturing techniques used to construct intracardiac devices from tubes or sheet metal (e.g. computer-aided design, laser cutting and so on) entirely ignore the thickness of the tube or sheet used. As a consequence, most, if not all devices of this type that have been so far produced have a constant thickness over their entire surface area. However, the present inventors have found that it is possible to modify the standard manufacturing techniques in order to produce an intracardiac device that has stabilizing elements with a thickness greater than the rest of said device. Such a device—as will be described in more detail hereinbelow—is thin enough such that it may be caused to adopt a crossing profile small enough for packing into a delivery catheter (by crimping), and which also possesses stabilizing elements (wings, arms etc.) that are able to better withstand fatigue, as a result of their greater thickness. It is to be noted, however, that in order for the thicker stabilizing elements not to interfere with the crimping of a dual-thickness (or variable thickness) device, the position of said elements within the sheet of metal used to manufacture the device must be carefully planned, such that these elements do not contribute to the overall diameter of the crimped device.

Thus, in one aspect, the present invention is directed to an intracardiac device suitable in size and form for endovascular delivery to the mitral valve annulus, wherein said device comprises a device body and one or more stabilizing wings, wherein at least one portion of each of said wings has a thickness greater than that of said device body.

In one particularly preferred embodiment of the present invention, said device is a cardiac valve support device suitable for endovascular delivery to the mitral annulus, and capable of providing a stable anchoring location for a subsequently-implanted replacement valve. Non-limiting examples of cardiac valve support devices that may be adapted to incorporate the stabilizing wing of the present invention are disclosed in co-owned, co-pending international patent application no. PCT/IL2013/000025 (published as WO2013/128436), which discloses and claims a single-ring device, as well as in co-owned, co-pending international patent application no. PCT/US2011/050232 (published as WO2012/031141) which discloses and claims a two-ring device. The contents of these publications are incorporated herein, in their entirety. It is to be recognized, however, that other types of device suitable for implantation at the mitral annulus and which include the thickened stabilizing wings disclosed above and described in more detail hereinbelow, also fall within the scope of the present invention.

A specific example of another type of device is a prosthetic valve (for example a stented prosthetic valve—examples of which may include a self-expanding prosthetic valve from a biocompatible metal such as Nitinol, or a balloon-expandable prosthetic valve, from a metal such as stainless steel or cobalt chromium). It should be noted that for the purposes of the present disclosure, the stabilizing wings may be characterized by three dimensions, the largest of which is defined as the length, the second-largest as the width, and the smallest dimension as the thickness of said arms. It is also to be noted that for the purpose of the present disclosure, the 'body' of the device is defined as all portions of the device except for the stabilizing wings or other stabilizing elements.

In one preferred embodiment of the present invention, each stabilizing wing, along its entire length and width, has a uniform thickness that is greater than the thickness of the body of the device.

In other preferred embodiments, different portions of each stabilizing wing differ with regard to their thickness. In some of these embodiments, the transition between a region of one thickness and a neighboring region having a different thickness may either by a discrete, step-like increase or decrease in thickness. In other cases, the transition may be in the form of a smooth, gradual increase or decrease in thickness.

In some preferred embodiments, the difference between the thickness of the device body and the maximum thickness of the device body is in the range of 0.05 mm to 0.6 mm. However, thickness differences that deviate from this range may also be used to work the present invention and therefore fall within the scope thereof.

By way of example, in one preferred embodiment of the present invention, the body of the intracardiac device has a thickness of 0.4 mm, while the stabilizing wings have a uniform thickness of 0.6 mm or 0.7 mm.

The present invention also provides a method for producing the above-disclosed device, comprising the steps of manufacturing a variable-thickness intracardiac device as disclosed hereinabove, wherein said process comprises the steps of:
 a) Marking out of origin points in the production layout.
 b) Selective reduction in thickness of selected regions of a metal sheet, on the basis of the final layout;
 c) Laser cutting of the layout on the thickness-processed sheet obtained from step (b);
 d) Preparation of the final product form using mandrels and heat treatment.

Preferably (but not exclusively) the metal sheet used to produce the device of the present invention is a medical-grade Nitinol sheet.

Preferred embodiments of the invention will now be described in more detail with the aid of the accompanying drawings, all of which relate to a single-ring mitral valve support device incorporating the variable thickness feature of the present invention. It is to be emphasized that the relation to a mitral valve support is for example only, and the invention may similarly be applied to other types of cardiac devices, with a specific example of such another type of device being a prosthetic valve (for example a stented prosthetic valve—examples of which may include a self-expanding prosthetic valve from a biocompatible metal such as Nitinol, or a balloon-expandable prosthetic valve, from a metal such as stainless steel or cobalt chromium). Thus, FIG. 1 illustrates a prior art single-ring valve support device comprising anchoring arms which are capable of applying both relatively weak forces to the ventricular wall during the first stage of the two-step implantation procedure and then stronger forces during the second stage of said procedure. In order to achieve this technical effect, the device, in this implementation comprises a single support ring to which are attached two or more anchoring wings which initially curve in an inferio-medial direction (i.e. towards the center of the internal space of the support ring. Then, the direction of the curvature of said wings changes such that they curve inferio-laterally, laterally, superio-laterally and then in a superior direction, finally ending in a short portion that curves back in a medial and inferio-medial direction. During the first stage of the implantation procedure, the curved wings are capable of applying relatively weak stabilizing forces to both the lateral wall of the ventricular cavity, as well as the tissue forming the roof of said cavity. Then, during and following expansion of a stented replacement valve within the central cavity of the support ring, the curved wings of the support device are pushed outwards and (as result of their curvature) upwards, such that they are capable of exerting much stronger forces on the ventricular tissue.

In the implementation of the mitral support device 10 shown in FIG. 1, the medial ends of the curved anchoring wings 14 are attached to the support ring 12, while the lateral ends of said wings are seen to curve outwards and, ultimately, upwards. The device depicted in this figure is in its fully-expanded state (i.e. following expansion of the replacement valve which would be placed within the central cavity of the support device), and the lateral ends of anchoring wings 14 are shown as if they are in a plane above the plane of support ring 12. However, in reality, in view of the pre-load on said wings, the lateral ends thereof would in fact come to rest in approximately the same plane as the support ring, and would apply strong axially-directed stabilizing forces to the tissues of the ventricle.

In the present invention, wings 14 are constructed such that they are thicker than the body of the device. In one preferred, non-limiting, example of the present invention, said wings have a uniform thickness of 0.6 mm, while the device body (i.e. the support ring) has a thickness of 0.4 mm. However, as explained hereinabove, other values for the thickness of the wings and device body are also included within the scope of the present invention.

Figure 2:
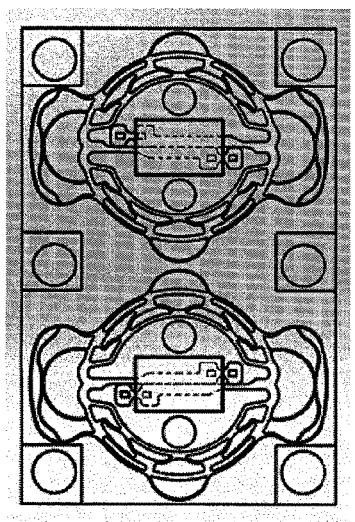
FIG. 2 presents a plan view of the layout of a variable thickness valve support device of the present invention, marked out on a Nitinol plate.

FIG. 2 shows a plan view of a layout of a device of the present invention marked out on a Nitinol plate. The large holes cut in the sheet (which are formed in regions which are not destined to become incorporated into the device itself) are used to provide points of origin, in order to direct the subsequent thickness-step.

Figure 3:
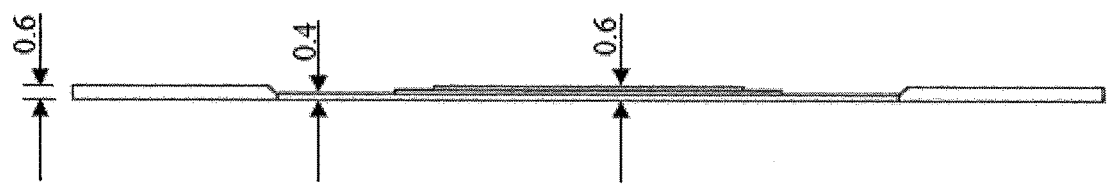
FIG. 3 shows a side view of a layout of the device depicted in FIG. 2.

FIG. 3 provides a side view of a layout of a device of the present invention in a Nitinol plate (as shown in FIG. 2) following thickness reduction. It will be noted that in the example shown in this figure, at the ends of the plate (i.e. outside of the region where the device design is located), the thickness of the metal is 0.6 mm: this corresponds with the initial overall thickness of the plate. Moving from either end towards the center of the plate, the thickness has been reduced to 0.4 mm: this is the region of the design in which the body of the device is located.

The next stage in the manufacturing process is to cut out the thickness-adjusted flat device by means of, for example, laser cutting. This essentially two-dimensional device (albeit with differences in "height", i.e. thickness in different regions thereof) is then manipulated into the desired three-dimensional shape on one or more mandrels using heat treatment. Finally, a series of post-processing steps—such as sandblasting in order to remove surface oxide layers and electropolishing—are used in order to prepare the finished product.

Figure 4:
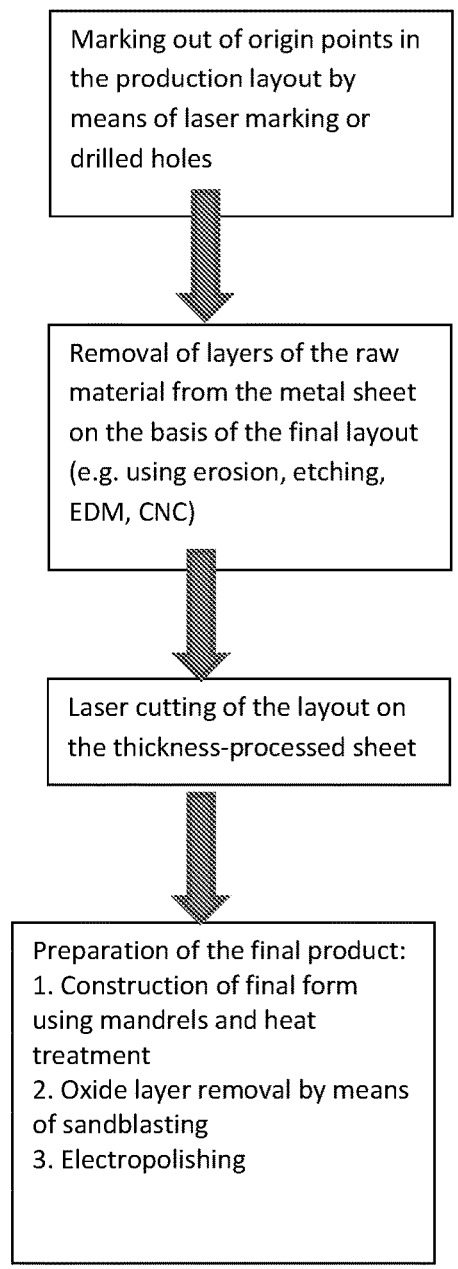
FIG. 4 schematically summarizes the various stages of the process for manufacturing a variable-thickness intracardiac device of the present invention.

All of the various stages in the above-described process for the manufacture of the variable-thickness device of the present invention are summarized in FIG. 4.

Figure 5:
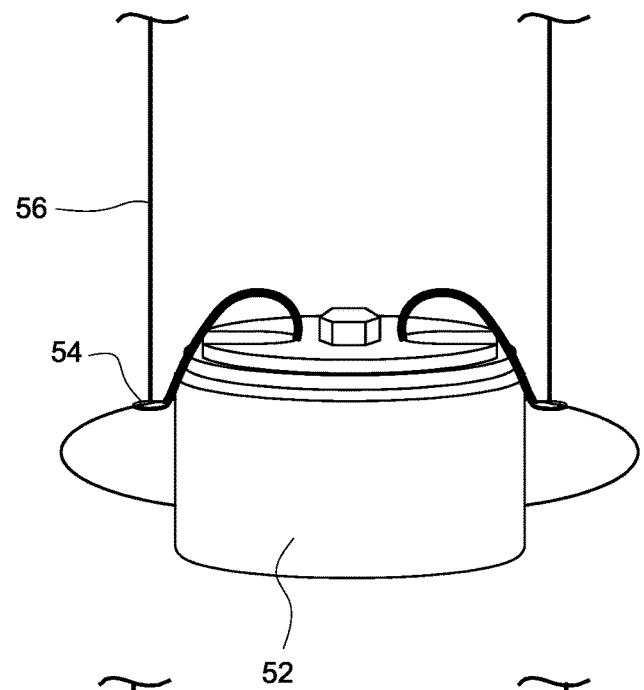
FIG. 5 is a photographic representation of variable thickness intracardiac device of the present invention held within an apparatus designed to measure the force required in order to achieve defined degrees of axial displacement of the stabilizing wings of said device, wherein said wings are shown in their starting position.

In order to investigate the effect of incorporating thickened stabilizing wings on the mechanical properties of a single-ring mitral valve support device, the following two devices were compared with respect to the magnitude of the axial tension forces that need to be applied to the distal ends of their wings in order to cause defined increments in axial displacement of the wing tips:

1) Prior Art Device:
   Body of device: thickness 0.4 mm. Stabilizing wings: thickness 0.4 mm
2) Device of the Present Invention:
   Body of device: thickness 0.4 mm. Stabilizing wings: thickness 0.55 mm As show in FIG. 5, each device was tested by means of placing it in a holder 52, such that the device body (not seen in this figure) was firmly retained by the holder, while the stabilizing wings 54 pass outwards and upwards through apertures in the roof of said holder. Tensioning wires 56 were attached to the distal ends of wings 54. These wires were then connected to a mechanism which is able to pull upwards on the wings, thereby causing axial displacement (in 0.25 mm increments) and to measure the force required in order to achieve each degree of displacement. FIG. 5 shows the stabilizing wings 54 in their starting position, that is, prior to the application of any tension thereto.

Figure 6:
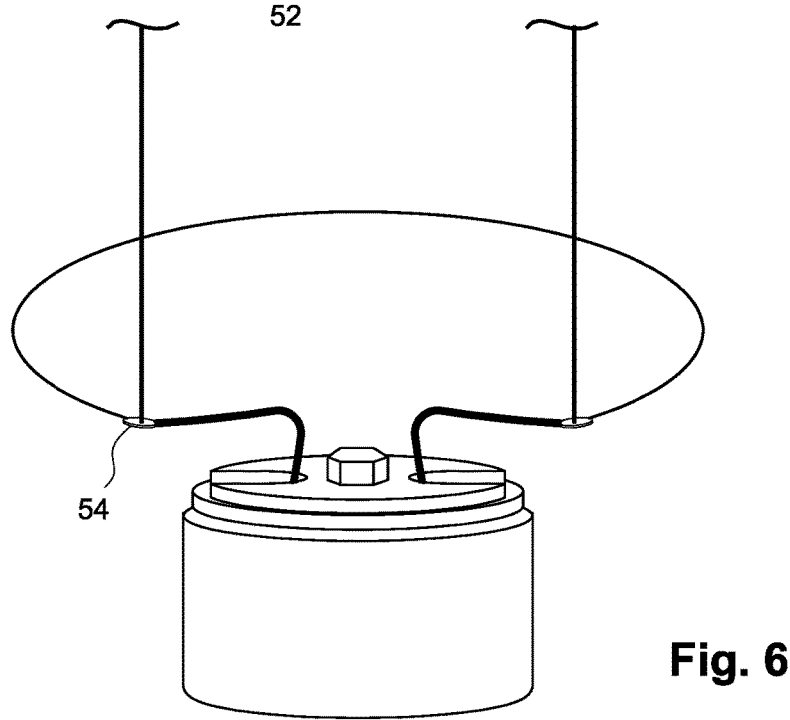
FIG. 6 shows the same test set-up as in FIG. 5, but following the application of a tensioning force to the stabilizing wings of the intracardiac device.

FIG. 6 shows the same test set-up as in FIG. 5, but after a tensioning force had been applied by the test device to the stabilizing wings 54. It will be noted that the wings 54 have been displaced upwards in an axial direction (i.e. in the plane of the longitudinal axis of the valve support device.)

Figure 7:
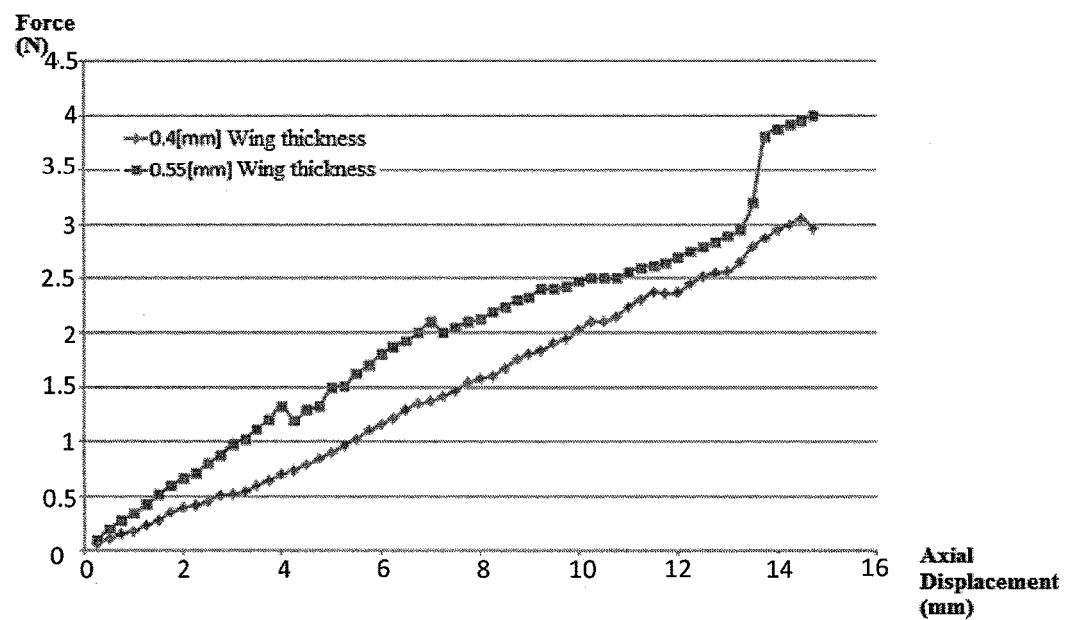
FIG. 7 graphically compares the force-displacement relationship obtained with two different devices of the present invention: one having a 0.55 mm wing thickness, and the other a 0.4 mm wing thickness.

This test set-up was used to measure the magnitude of the pulling (tension) forces required in order to achieve a particular axial displacement of the wings. The results of this test for the two stabilizing wings being compared (as described above) are shown in FIG. 7, in which the upper curve corresponds to the device of the present invention (0.55 mm wing thickness), while the lower curve presents the results for the prior art device (0.4 mm wing thickness). It will be seen from this figure that the force/displacement curve shifts to the left when a thicker wing profile is used, indicating that said thicker wing applies a greater axial preload force than the thinner wing, for any given axial displacement. It may thus be concluded that the thicker stabilizing wing is better able to withstand the displacing forces applied to it by the contracting heart, and will thus be better able to withstand fatigue over time.

As described hereinabove, the device of the present invention is generally prepared from sheet Nitinol having a starting thickness of between about 0.4 mm and about 0.8 mm (although other thicknesses are also possible and fall within the scope of the invention). While the stabilizing wings are generally cut out of the same metal sheet as the body of the valve support device (as described above), in some embodiments said wings maybe constructed separately from Nitinol sheet, wire or tubing and then welded or soldered onto the support ring.

Typically, the outer diameter of the support element of the support ring of the presently-disclosed cardiac valve support device will be in the range of 23-60 mm, while its inner diameter will have a value in the range of 23-35 mm. Devices having diameters smaller or larger than the limits of these ranges may also be required in certain circumstances, and are included within the scope of the present invention.

Additionally, as previously explained the device of the invention may be a prosthetic valve which is to be placed in the annulus and anchored in place by the anchoring element of the invention.

The delivery and implantation of the devices illustrated and described herein may be achieved by endovascular and transapical methods, as described in detail in many publications including WO2013/128436 and WO2012/031141.

The device of the invention is described herein mainly in the context of the mitral valve of the left ventricle. However, this is intended as a non-limiting example, and the device may similarly be used in the position of the tricuspid valve, between the right atrium and right ventricle, or in other positions such as the aortic or pulmonary valve positions.

Second Main Embodiment

In this aspect, the present invention is directed to a device suitable in size and form for transcatheter delivery to the mitral valve annulus, wherein said device comprises a device body and one or more stabilizing wings, wherein each of said wings comprises one or more primary anchoring arms, the purpose of which is to apply upwards (wherein in this example—"upwards" refers to a force which is directed from the ventricle towards the atrium) axially-directed stabilizing forces onto the tissues at or near the mitral annulus, preferably in the region of the valve commissures, and one or more auxiliary arms, the purpose of which is to reduce the strain on the primary anchoring arm(s) following deployment of said device. The stabilizing wings will generally also comprise one or more connecting arms for connecting the aforementioned arms to the device body.

The general arrangement of the various components of the stabilizing wings of the present invention will now be described.

Thus, each of said stabilizing wings preferably comprises a connecting arm that is oriented essentially vertically downwards (wherein in this example "downwards" refers to a direction from the atria to the ventricle) with respect to the device body, having a distal extremity ending at a first branch point, and a proximal end continuous with said device body. The stabilizing wing distal to said first branch point comprises the following two arms:
1) Primary anchoring arm which passes laterally, with its distal end above and lateral to the outer surface of the device body. The function of this arm is to provide support for the device body by means of applying axially-directed forces on the tissues of the ventricle in the vicinity of the mitral valve annulus.
2) Primary support arm which passes medially and generally either axially upwards or axially downwards. The distal end of said primary support arm is located at a distance from the imaginary center of the generally-circular device body that is approximately equivalent (+1-4 mm) to the position of said device body. The function of the primary support arm is to reduce the total stress and strain exerted by the contracting heart on the aforementioned primary stabilizing arm.

In preferred embodiments of the present invention the aforementioned first branch point is characterized in having a circular, elliptical or other rounded aperture which separates the proximal end of the primary support arm from the distal end of the connecting arm. In a particularly preferred embodiment, said aperture is elliptical.

Optionally, in certain embodiments, the stabilizing wing of the present invention may further comprise a secondary branch point, which may be located on the connecting arm, the primary stabilizing arm or the primary support arm. The stabilizing wing distal to said secondary branch point comprises the following two arms:
A) The continuation of the arm (connecting arm or primary stabilizing arm or primary support arm) from which the secondary branch point arises; and
B) Secondary support arm which passes medially from the secondary branch point (i.e. generally in the opposite direction to the primary anchoring arm). The main purpose of the secondary support arm is to reduce the stress and strain exerted by the contracting heart on the arm from which said secondary support arm arises.

In some preferred embodiments of the stabilizing wing of the present invention, one or more of the connecting arm, the primary support arm and/or the secondary support arm are covered with a polymeric sleeve, the purpose of which is to act as a "shock absorber" for said stabilizing wing, by means of absorbing some of the stress exerted on the covered arm(s) into said sleeve. While any suitable biocompatible polymer may be used to construct said sleeve, preferred embodiments thereof include silicone, PTFE and PE.

The device of the present invention may comprise one or more stabilizing wings. In a preferred embodiment, the device comprises two such wings. Each of said stabilizing wings comprises one or more primary anchoring arms. Similarly, each wing comprises one or more primary support arms. Optionally, each stabilizing wing may further comprise one or more secondary support arms.

In one particularly preferred embodiment of the present invention, the aforementioned device is a cardiac valve support device suitable for endovascular delivery to the mitral annulus, and capable of providing a stable anchoring location for a subsequently-implanted replacement valve. Non-limiting examples of cardiac valve support devices that may be adapted to incorporate the stabilizing wing of the present invention are disclosed in co-owned, co-pending international patent application no. PCT/IL2013/000025 (published as WO2013/128436), which discloses and claims a single-ring device, as well as in co-owned, co-pending international patent application no. PCT/US2011/050232 (published as WO2012/031141) which discloses and claims a two-ring device. The contents of these publications in their entirety are incorporated herein.

As indicated above, the valve support devices disclosed in WO2013/128436 and WO2012/031141 are intended for use in two-stage procedures wherein the first stage comprises the delivery and implantation of a valve support at a cardiac valve annulus, and the second stage comprises the implantation of a replacement cardiac valve within the central space of said valve support. When the stabilizing wings of the present invention are incorporated as part of a support device of this type, in most embodiments, the support arm (or at least the distal end thereof) is in contact with the outer wall of said replacement valve. Similarly, in most preferred embodiments of the present invention in which a secondary support is present, said arm is preferably oriented in the same as the outer surface of the replacement valve, and is in contact therewith. However, different spatial orientations of the secondary support arm are also possible and are within the scope of the present invention. In one preferred embodiment, the secondary support arm is orientated such that is approximately parallel with the horizontal plane of the device body and makes contact along part or all of its length with the replacement valve.

It is to be recognized that in addition to the valve support devices mentioned hereinabove, other types of device suitable for implantation at the mitral annulus and which include stabilizing wings comprising the primary anchoring arms and auxiliary arms disclosed above and described in more detail hereinbelow, also fall within the scope of the present invention. A specific example of another type of device is a prosthetic valve (for example a stented prosthetic valve—examples of which may include a self-expanding prosthetic valve from a biocompatible metal such as Nitinol, or a balloon-expandable prosthetic valve, from a metal such as stainless steel or cobalt chromium).

Without wishing to be bound by theory, it is believed that the presence of one or more auxiliary arms allows for "sharing" of the total strain exerted by the contracting heart on the device between said auxiliary arm(s) and the primary anchoring arms, thereby reducing the strain on each of said arms to below a potentially-damaging value. Several different mechanisms may be responsible for this strain-sharing effect, including (but not limited to) a change in the bending geometry of the primary arm, a vector of the total strain being taken up by the auxiliary arm and so on.

The detailed description in the following section relates to mitral valve support devices that incorporate various embodiments of the stabilizing wings of the present invention.

In order to more fully understand the structure of the novel stabilizing wing of the present invention, it is useful to compare this wing with examples of a prior art single-ring mitral valve support devices intended for implantation at the mitral annulus. One such example is illustrated in FIG. 1, and was described in detail hereinabove.

Figure 8:
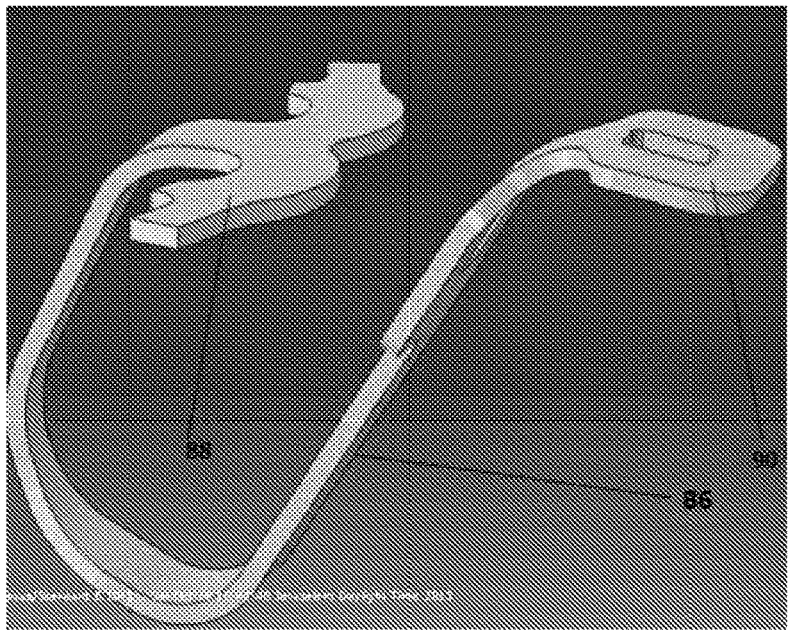
FIG. 8 depicts a further example of a stabilizing wing that forms part of a prior art intracardiac device.

FIG. 8 depicts another example of a prior art stabilizing arm 86, having a flattened distal portion 90 for contacting the ventricular tissues in the commissural region, and applying axially-directed forces thereto, and a proximal extremity 88 which is continuous with (and/or connected to) the body of the mitral valve support ring.

Figure 9:
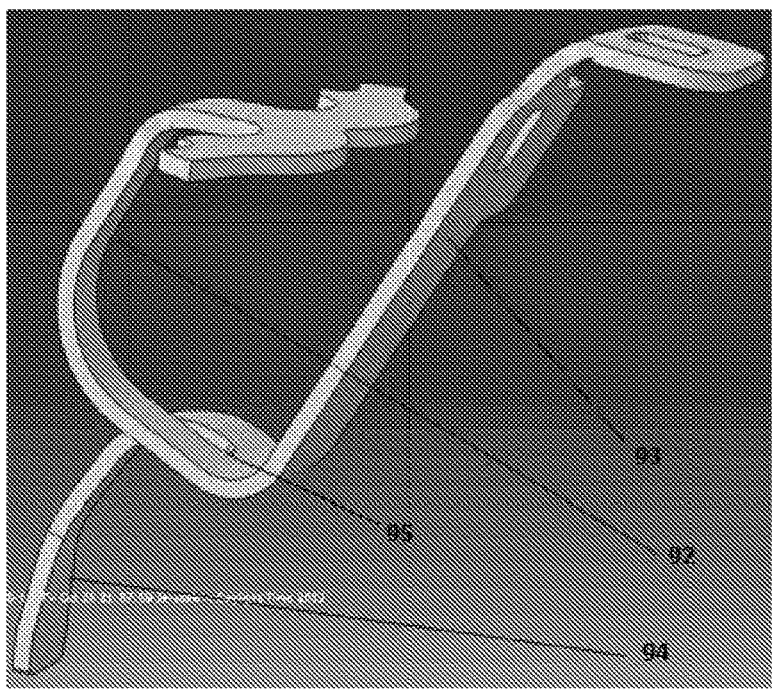
FIG. 9 illustrates one embodiment of a stabilizing wing of the present invention comprising a primary anchoring arm, a primary support arm and a connecting arm.

FIG. 9 illustrates one embodiment of a stabilizing wing of this aspect of the present invention. It may be seen that this wing differs from that of the prior art device shown in FIGS. 1 and 8, in that the stabilizing wing of this embodiment of the present invention comprises three distinct elements: a primary anchoring arm 93 (which is comparable in structure and function with stabilizing arm 86 of the prior art device shown in FIG. 8), a primary support arm 94, which is disposed such that its free distal end points inferiorly, in a direction that is nearly opposite to that of primary anchoring arm 93, and a connecting arm 92, which at its upper end is continuous with (or connected to) the body of the mitral device (not shown). It may be seen that these three arms meet at branch point 95.

Figure 10:
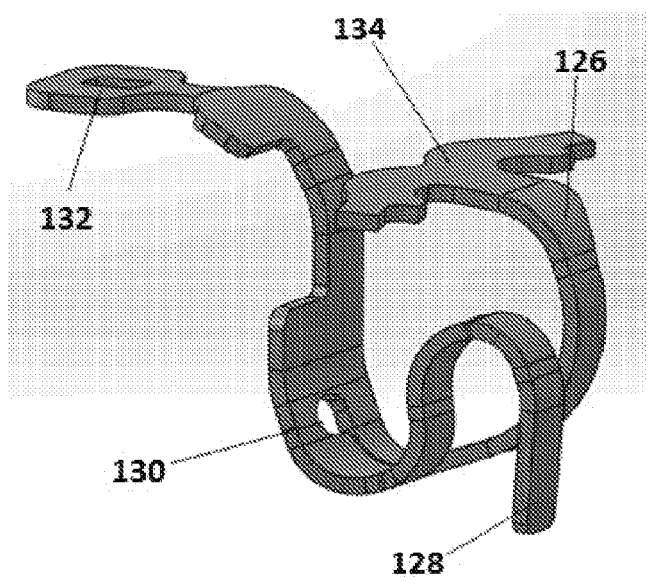
FIG. 10 depicts a further embodiment of a stabilizing wing of the present invention, wherein said wing comprises a primary anchoring arm and a primary support arm, both of which arise from a common branch point.

A similar embodiment of the present invention is shown in more detail in FIG. 10. In this figure, it may be clearly seen that the primary anchoring arm 132 and primary support arm 128 both arise from branch point 130, which in turn is connected to the body of the support device 134 by the proximal end of connecting arm 126. Also shown in this figure is the flattened distal end 132 of the primary anchoring arm, which is designed to make atraumatic contact with the tissue of the ventricular roof. This figure also illustrates the preferred elliptical form of the aperture created at branch point 130.

Figure 11:
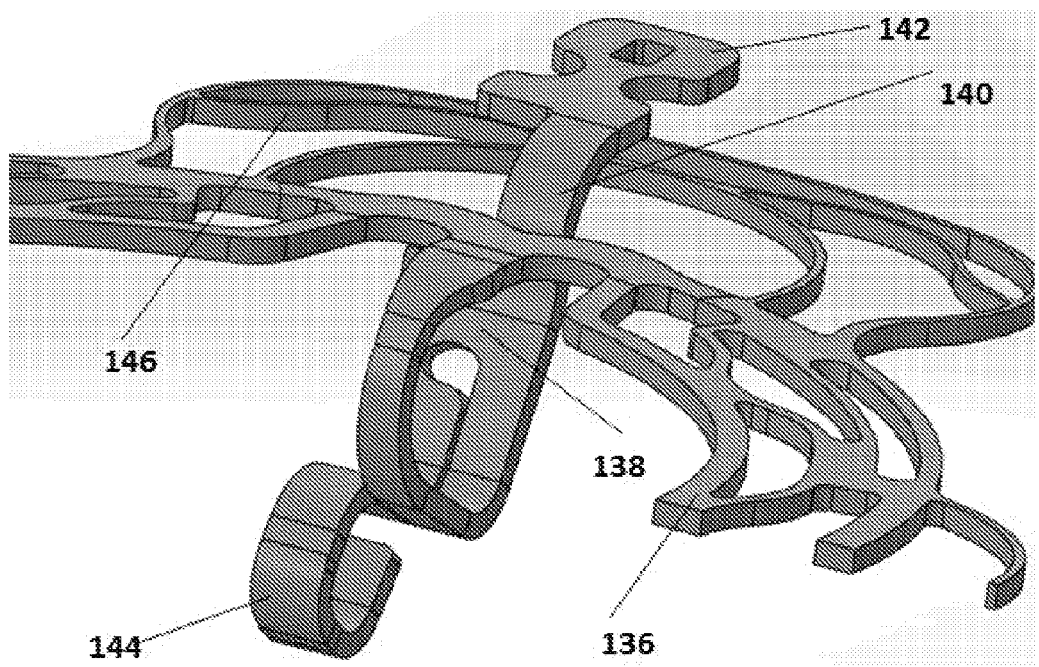
FIG. 11 provides a perspective view of a further embodiment of a cardiac valve support device fitted with primary anchoring and support arms, in which said arms are connected by a connecting arm to the ring-like device body.

FIG. 11 depicts a further embodiment of the present invention. In particular, this figure illustrates the manner in which the primary anchoring and primary support arms (140 and 144, respectively) are connected by the connecting arm 138 to the ring-like support device body 136. This figure also illustrates another embodiment of the primary anchoring arm distal end 142, as well as an additional lateral extensions 146, which are intended to be deployed above the mitral valve commissures, in such a way that they "cover" the space formed by the commissures (thereby preventing paravalvular leakage), as well as providing additional stabilization for the valve support device.

Figure 12:
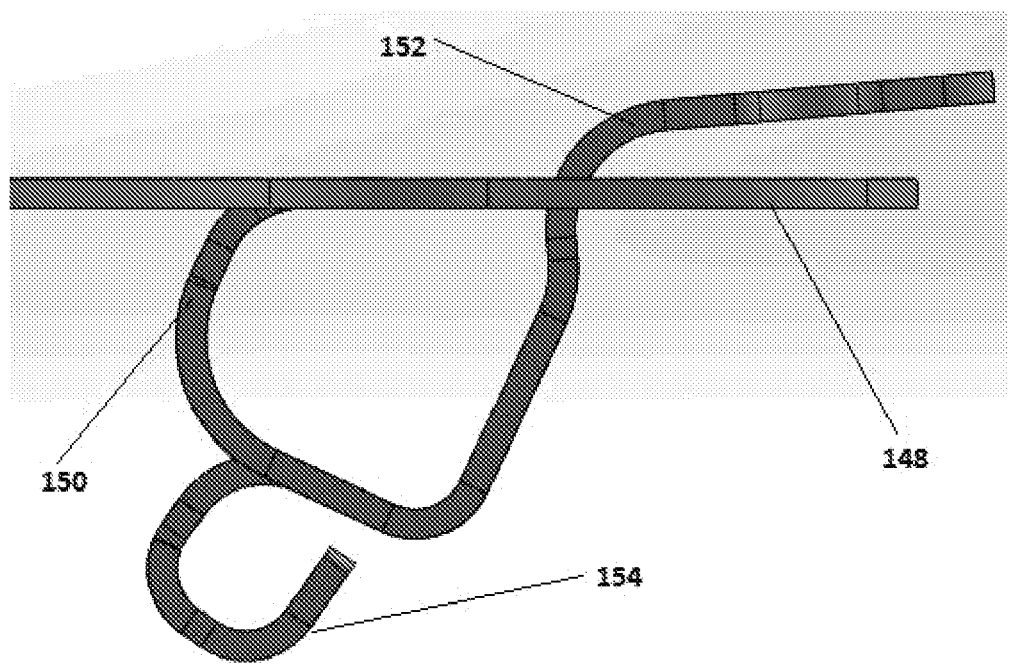
FIG. 12 presents a side view of the embodiment depicted in FIG. 11.

FIG. 12 provides a side view of the embodiment of the device shown in FIG. 11, with primary anchoring and primary support arms (152 and 154 respectively) being connected to the valve support ring 148 by means of connecting arm 150.

Figure 13:
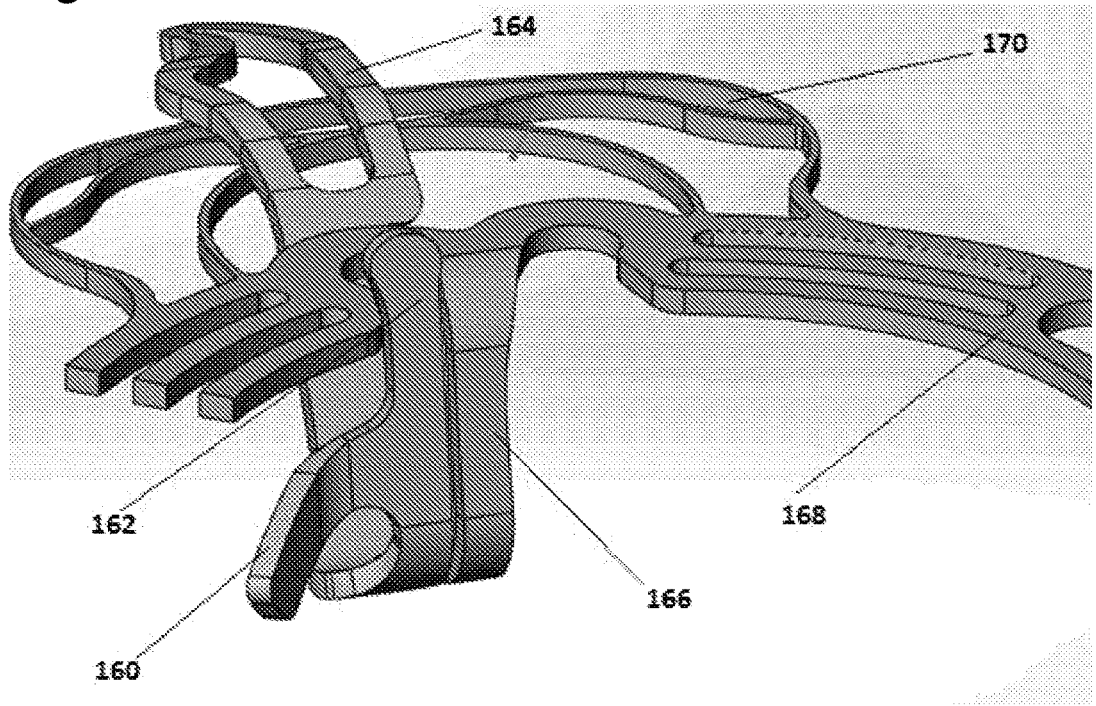
FIG. 13 provides a perspective view of a further embodiment of a valve-support device of the present invention, in which the anchoring or stabilizing wing comprises a secondary support arm in addition to a primary support, anchoring arm and connecting arm.

FIG. 13 presents a perspective view of a different embodiment of the present invention, in which a secondary support arm 160 arises at a second branch point located on the primary support arm 162. This drawing also clearly shows the manner in which both the primary and secondary support arms (160 and 162) are orientated in the opposite direction from the primary anchoring arm 164. For the sake of completeness, FIG. 13 also shows the connecting arm 166 which connects the other arms to the device body 168. It will also be noted from this perspective view that the primary support arm 162 and connecting arm 166 are arranged side-by-side, with a narrow groove between them. Additional lateral extensions 170, similar to those of FIG. 11, are also shown in the figure.

Figure 14:
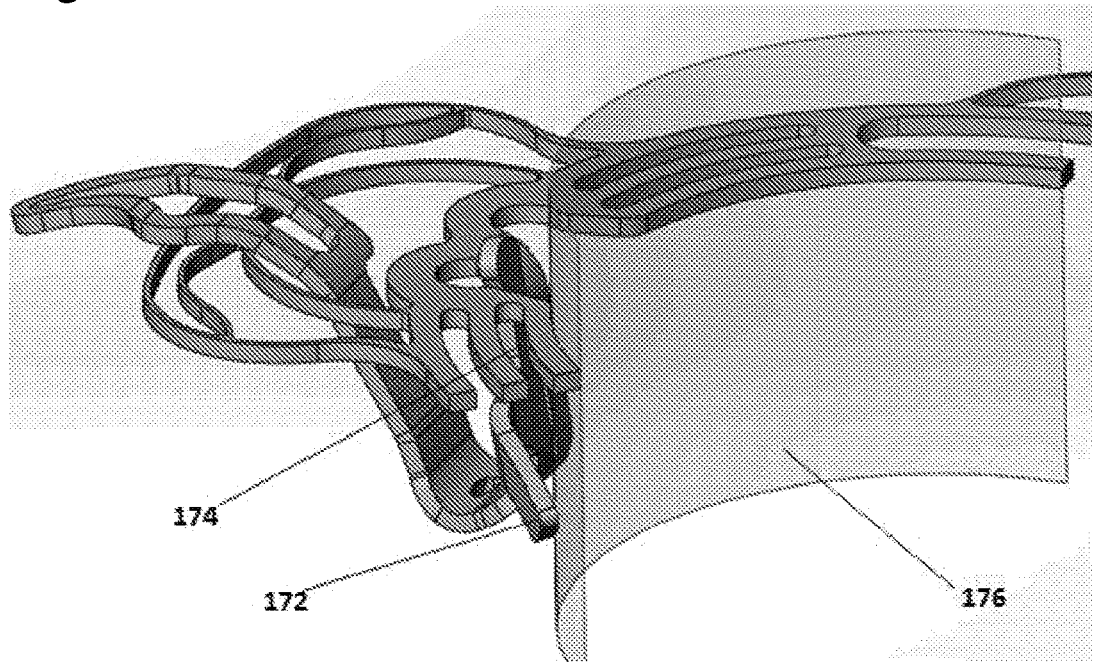
FIG. 14 provides another perspective view of the embodiment of FIG. 13, in which the position of the outer surface of a replacement cardiac valve is indicated by a curved plane.

FIG. 14 shows another perspective view of the embodiment illustrated in FIG. 13, in which the position of the outer surface of a replacement cardiac valve is indicated by the curved plane 176. It will be noted that both the primary and secondary support arms (174 and 172, respectively) may be in physical contact with this plane, and hence with the replacement valve, following implantation.

Figure 15:
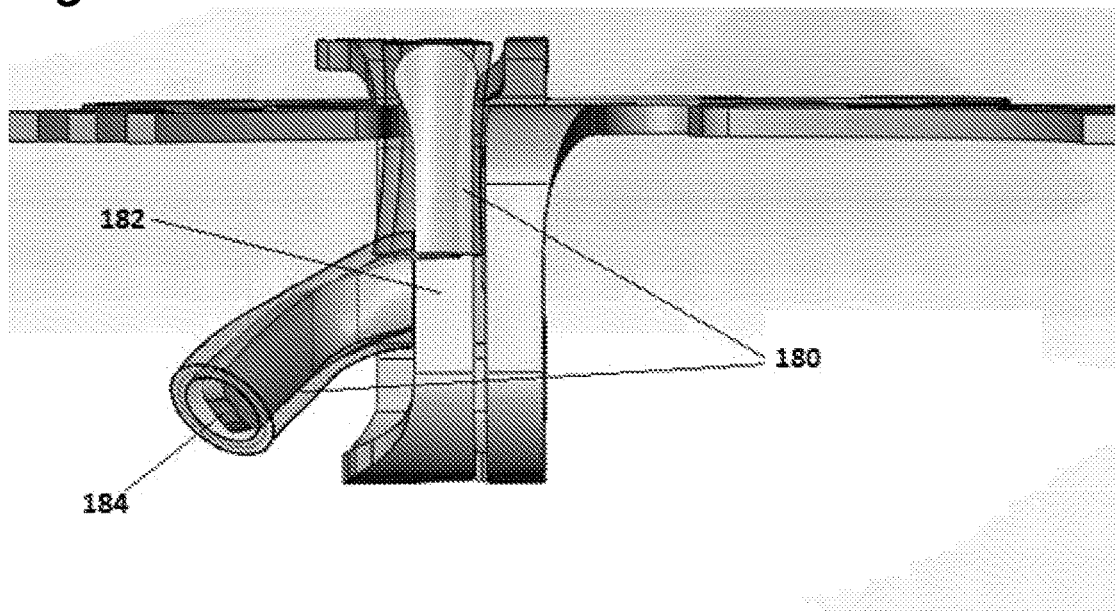
FIG. 15 presents a front view of the same embodiment that was shown in FIGS. 13 and 14, but which further comprises shock-absorbing polymeric sleeves for the support arms.

FIG. 15 provides a front view of the same embodiment that was shown in FIGS. 13 and 14. In this case, however, the primary 182 and secondary 184 support arms are covered with shock-absorbing sleeves constructed from a biocompatible polymer (for example, silicone) 180.

Figure 16:
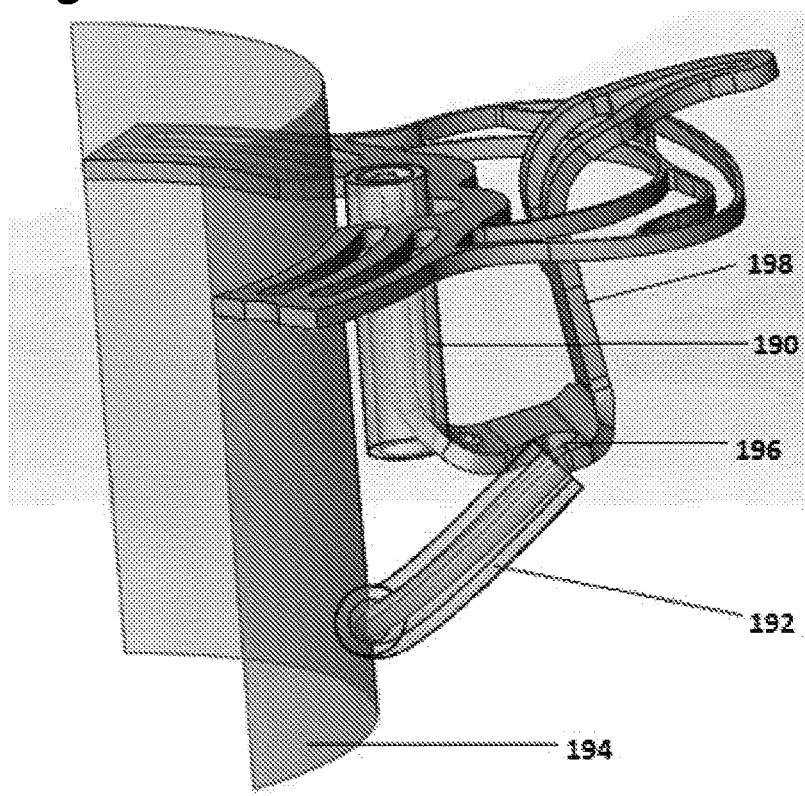
FIG. 16 depicts an alternative embodiment of the present invention, in which the secondary support arm arises from a second branch point located at the junction of the connecting arm and the primary anchoring arm.

FIG. 16 provides a perspective view of an alternative embodiment of the present invention, in which a secondary support arm 192 is seen arising from a second branch point 196 located at the junction of the connecting arm 190 and the primary anchoring arm 198. It may be appreciated that said second branch point 196 differs from the corresponding structure in the embodiment of FIGS. 13-15 by virtue of being a trifurcation, rather than bifurcation. Both the primary and secondary support arms in this figure are very close to, or in actual contact with, plane 194 which represents the position of the outer surface of a replacement cardiac valve, following implantation within the central space of the valve support device.

Figure 17:
FIG. 17 presents the results of a finite element analysis (FEA) of a valve support stabilizing wing of the present invention, in which said wing comprises a primary anchoring and primary support arm. The FEA results shown in this figure were obtained immediately after implantation of the valve support device at the mitral annulus.
Figure 18:
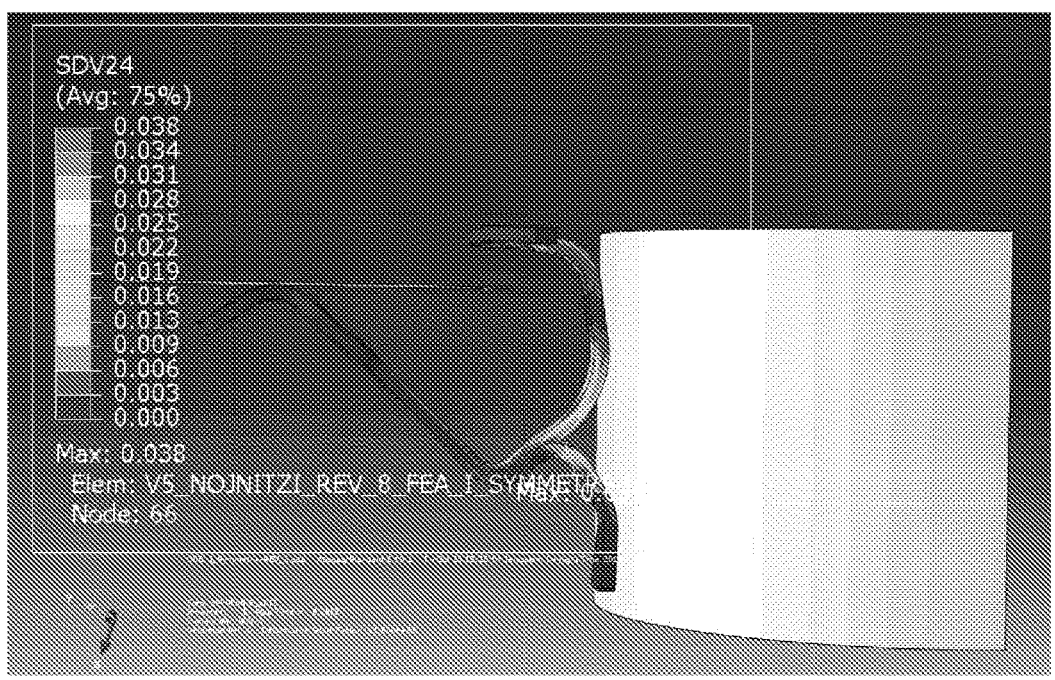
FIG. 18 presents FEA results for the same device used to generate the results of FIG. 17, but which were obtained during systolic contraction of the ventricle.

Finite element analysis (FEA) was used in order to demonstrate the reduction in the strain exerted on the primary anchoring arm as a consequence of the presence of an auxiliary arm (i.e. a primary support arm). For the purposes of the present study, FEA was performed using Abaqus 12.1 software, by Static Study with Implicit Solver. The simulation was defined using in-vivo boundary conditions that include contact interactions between different parts. Simulation was performed without global or contact stabilization and damping effects, which might influence numerical results. Material properties were defined based on environment controlled uni-axial tests and implemented by a UMAT subroutine. FIGS. 17 and 18 present the results of the FEA of a stabilizing wing of the present invention, and illustrate the way in which the maximal strain is transferred from the primary anchoring arm to the primary support arm. In these figures, the horizontal plane situated immediately above the free upper end of the primary arm (and in contact therewith) represents the height at which said upper end is located in relation to the rest of the device, while the partial cylinder (on the right of each figure) represents the surface bounded by the inner circumference of a single ring mitral valve support device, and therefore indicates the position of the replacement cardiac valve following its deployment and expansion within said inner circumference. FIG. 17 shows the valve support device immediately following implantation at the mitral annulus, with the maximal strain located in the central portion of the primary anchoring arm. Then, as shown in FIG. 18, during systolic contracture of the ventricle in which the loads are increased with the increased pressures in the ventricle, the maximal strain shifts from this position downwards to the primary support arm. It may be also be seen that, overall, the strain is now shared between the primary anchoring and support arms, rather than being concentrated in the primary anchoring arm only.

The results of this analysis therefore clearly demonstrate the reduction in strain load on the primary anchoring arms of the mitral device, thereby reducing the probability of fatigue, fracture and device failure.

In addition to the reduction in fatigue-inducing forces on the primary anchoring arm(s), the presence of the auxiliary (i.e. support) arm(s) is also advantageous in other ways. One such advantage is the increase in pre-load force that is exerted by the primary anchoring arm on the commissural tissue upon implantation. Thus, a stabilizing wing of the present invention (such as illustrated in FIG. 9) exerts a pre-load force which is higher than that of a prior art stabilizing wing (such as shown in FIG. 8), wherein the two stabilizing wings are of equal thickness. Furthermore, increasing the thickness of the presently-disclosed stabilizing wing results in still further increases in the value of the pre-load force. Details concerning the construction of stabilizing wings having a thickness different from the device body have already been provided hereinabove.

A second additional advantage conferred by the presence of the auxiliary arm(s) is that the force/deflection curve of the primary anchoring arm is altered (as compared with prior art stabilizing wings), such that after implantation, and an initial further movement of about 2-3 mm into the commissural tissue, any subsequent deflection of the primary arm does not result in any substantial increase in the force exerted by said primary arm on said tissue. In other words, the stabilizing wing of the present invention can be constructed such that following its initial movement into the ventricular tissue, the primary anchoring arm will exert a constant, atraumatic force thereon.

Figure 19:
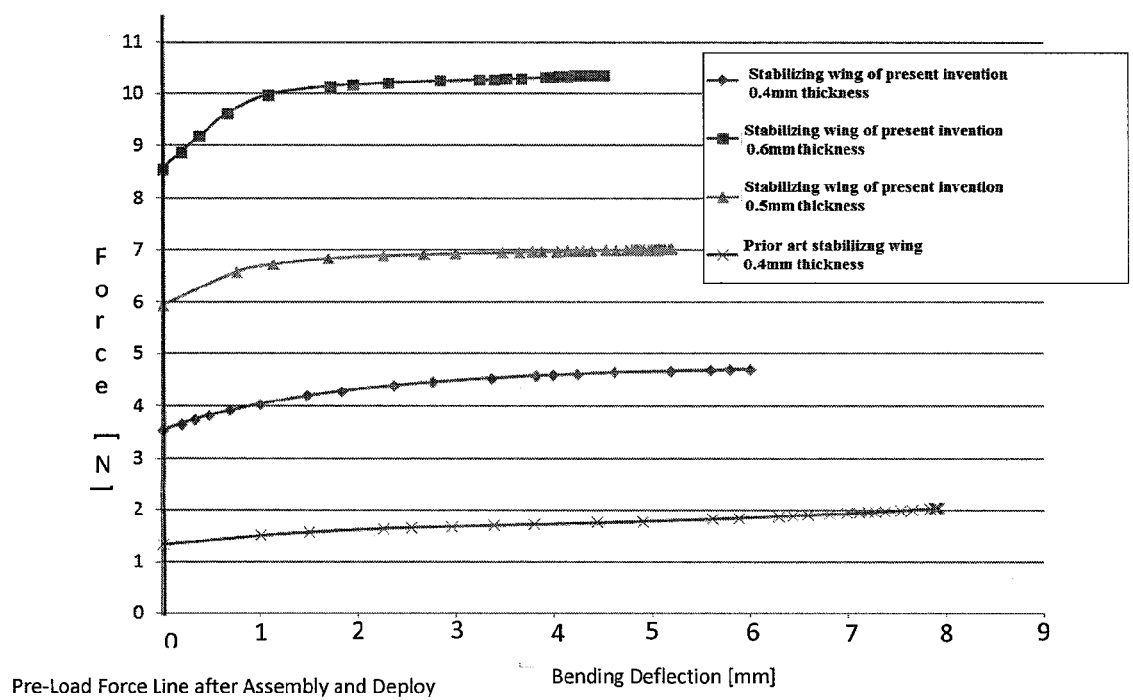
FIG. 19 graphically depicts the force/deflection relationship for embodiments of the present invention in which the stabilizing wing comprises a primary anchoring arm and a primary support arm. Three of the curves relate to devices of the present invention having wing thicknesses of 0.4, 0.5 and 0.6 mm, while the fourth curve relates to a prior art (0.4 mm) wing (i.e. lacking the support arm).

Both of these advantages are shown in FIG. 19 which presents a series of force/deflection curves for the presently-disclosed stabilizing wings of varying thicknesses (0.4, 0.5 and 0.6 mm), together with a curve for a prior art wing (0.4 mm thick). These curves were generated by means of a parametric numerical study of thickness change with constant boundary conditions mimicking in-vivo periodic load, and contacts definition and typical reaction force output for each study.

It may be seen from this graph that the values for the pre-load force (i.e. the force at 0 mm deflection) are significantly greater for the wing of the present invention than for the prior art wing. Furthermore, the pre-load value for the presently-disclosed wing increases with increasing thickness. The pre-load values for the various devices are summarized in the following table:

|  |  | Pre-Load Force after Assembly and Deployment [N] |
|---|---|---|
| Prior art device | 0.4 mm thick | 1.33 |
| Present invention | 0.4 mm thick | 3.54 |
| Present invention | 0.5 mm thick | 5.93 |
| Present invention | 0.6 mm thick | 8.55 |

FIG. 19 also illustrates the asymptotic nature of the force/deflection relationship of the device of the present invention (at all thickness), following an initial increase in force during the first 2-3 mm of deflection.

This embodiment of the cardiac support device of the present invention, as described hereinabove and illustrated in the accompanying figures, is generally constructed from medical-grade Nitinol sheet, preferably having a thickness between 0.25 and 1.2 mm. Other biocompatible metals having the desired shape-memory properties may also be used in place of Nitinol. Following layout of the intended design on the metal sheet, laser cutting is used to cut out said design. Subsequently, the final product is formed using heat treatment and mandrels, as is well known to skilled artisans in the field. Final processing stages may optionally include oxide layer removal by means of sandblasting and electropolishing. While the stabilizing wings are generally cut out of the same metal sheet as the body of the valve support device (as described above), in some embodiments said wings may be constructed separately from Nitinol sheet, wire or tubing and then welded or soldered onto the support ring.

Typically, the outer diameter of the support element of the support ring of the presently-disclosed device will be in the range of 23-60 mm, while its inner diameter will have a value in the range of 23-35 mm. Devices having diameters smaller or larger than the limits of these ranges may also be required in certain circumstances, and are included within the scope of the present invention.

Additionally, as previously explained, the device of the invention may be a prosthetic valve which is to be placed in the annulus and anchored in place by the anchoring element of the invention.

The delivery and implantation of the devices illustrated and described herein may be achieved by endovascular and transapical methods, as described in detail in many publications including WO2013/128436 and WO2012/031141.

This embodiment of the device of the invention (as will all of the other main embodiments described herein) is described herein mainly in the context of the mitral valve of the left ventricle. However, this is intended as a non-limiting example, and the device may similarly be used in the position of the tricuspid valve, between the right atrium and right ventricle, or in other positions such as the aortic or pulmonary valve positions.

Third Main Embodiment

In a further group of embodiments, the stabilizing wings of the intracardiac device further comprise additional elements that serve to improve their fatigue resistance during long-term use. Examples of such additional elements include: wire-covered wings, polymer-sleeve coated wings and wings fitted with leaf springs.

Thus, in one preferred embodiment of the intracardiac device of the present invention, the stabilizing elements comprise stabilizing wings having a wire coil wound therearound, wherein said wire coil serves to improve the fatigue resistance of said stabilizing wings. While a wire of any suitable material may be used for this embodiment, in one highly preferred embodiment, the wire used is a metal wire, most preferably a Nitinol wire. Alternatively, the wire may be manufactured from a biocompatible polymer including (but not limited to) polyester or Nylon. Preferably, the wire is tightly wound around the stabilizing wings such that there is no fluid-permeable space between the wire coil and said wings.

Generally, the wire used to cover the stabilizing wing has a diameter in the range of 0.1-1 mm.

Figure 20:
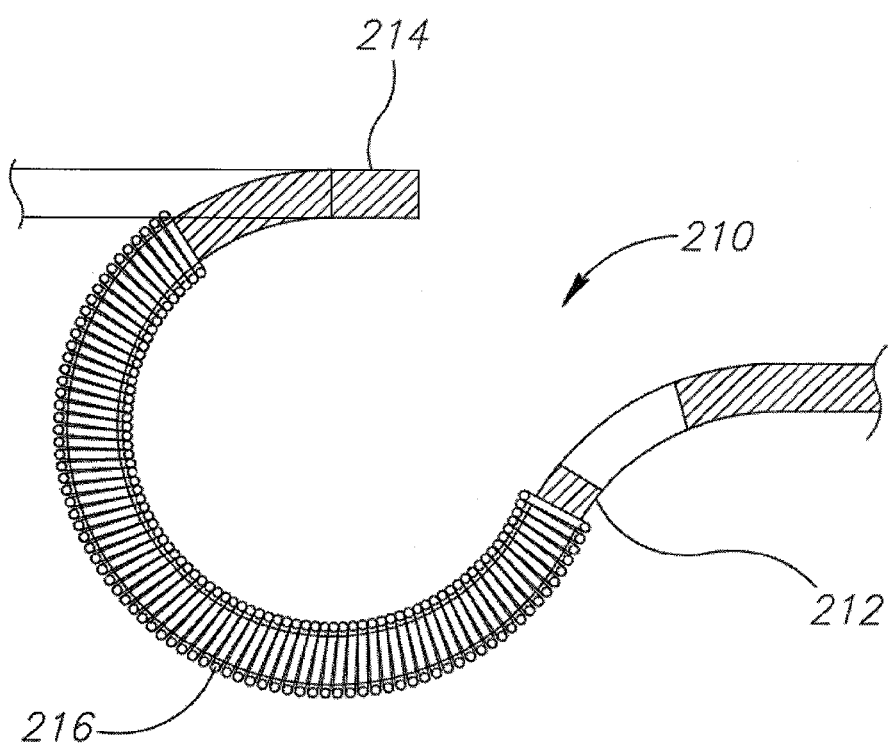
FIG. 20 provides a side view of an embodiment of a valve support device in which the stabilizing wing is partly covered with a Nitinol wire coil.

An example of an embodiment of the present invention comprising a Nitinol wire coil wrapped around an intracardiac device stabilizing wing is shown in FIG. 20. In this figure a portion of a mitral valve support device 210 is shown in transverse section. It may be seen from FIG. 20 that stabilizing wing 212 is attached at its medial end to part of the device body, which comprises an annular ring 214. Approximately half of the length of stabilizing wing 212 is covered with a tightly-wound Nitinol wire coil 216. In other embodiments, a larger or smaller proportion of the length of the wing may be covered by the wire coil.

In another preferred embodiment of this aspect of the present invention, the stabilizing elements comprise curved stabilizing wings having a leaf spring attached via one or both of its ends to the inner curvature of said wings. The attachment of the wire to the wing may be accomplished, for example, by laser welding, spot welding, sutures, mechanical attachment such as a rivet, circlip etc.

In most embodiments of this aspect of the invention, the curvature of the leaf spring conforms very closely to the inner curvature of the stabilizing wing. In other embodiments, the curvature of the leaf spring conforms very closely to the outer curvature of the stabilizing wing.

In most embodiments, the leaf spring is constructed from Nitinol, and generally has a length in the range of 1 to 15 mm, a width of 1 to 10 mm and a thickness in the range of 0.1 to 1 mm.

In some embodiments there can be a "separating element" between the metal elements, for example a biocompatible polymer such as polyester.

Figure 21:
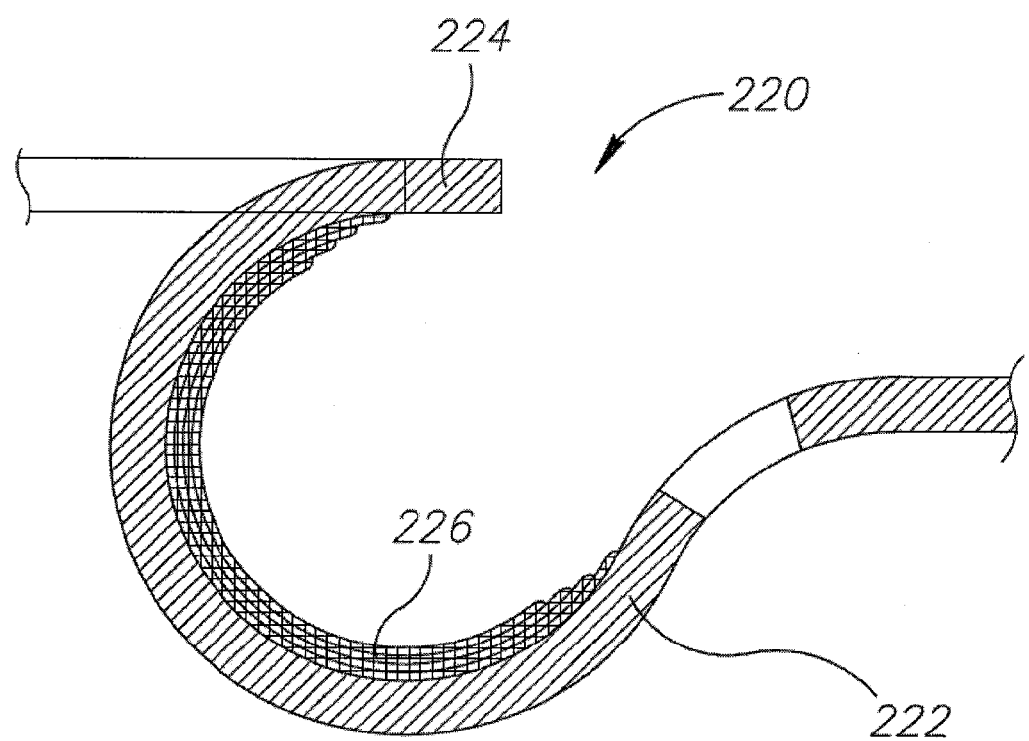
FIG. 21 depicts another embodiment of the present invention in which a stabilizing wing, attached to an annular valve support ring, has a leaf spring connected to its inner curvature.

FIG. 21 schematically illustrates an example of a valve support device 220 comprising a stabilizing wing 222 connected to an annular support ring 224. As seen in this figure, a Nitinol leaf spring 226 is connected to the inner curvature of said stabilizing wing.

Figure 22:
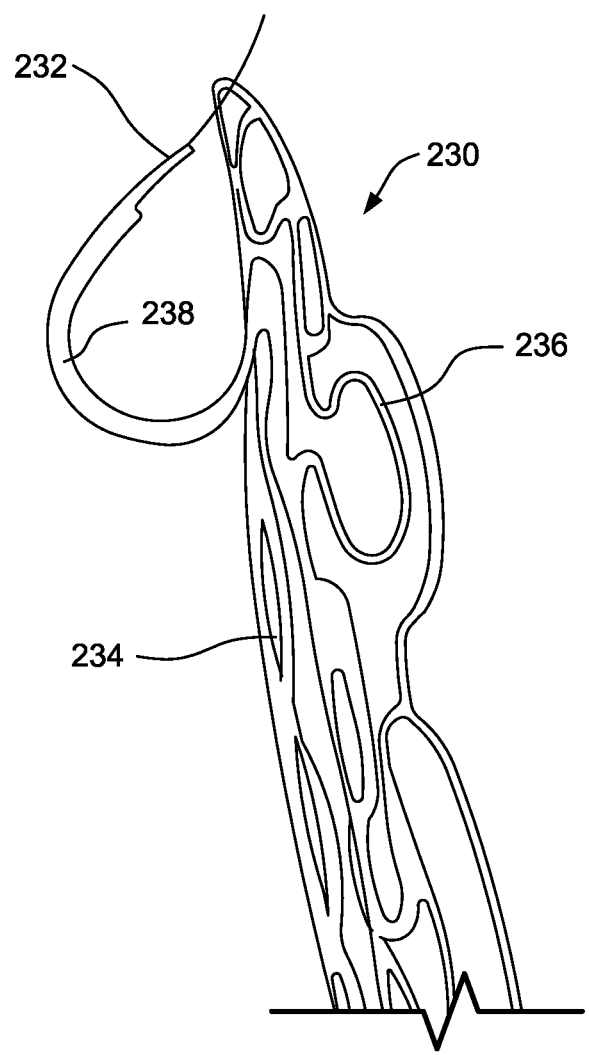
FIG. 22 provides another view of the same embodiment of the valve support device as shown in FIG. 21.

A similar embodiment of a valve support device, 230 is depicted in FIG. 22. As shown, said valve support device comprises a single annular support ring 234 and two stabilizing wings 232. A leaf spring 238 is seen attached to the inner curvature of one of the stabilizing wings. In addition, this figure also illustrates a crown-shaped lateral extension 236 extending outwards from support ring 234.

In a further preferred embodiment of this aspect of the present invention, the stabilizing elements comprise curved stabilizing wings which are coated with an elastic polymer. Exemplary polymers include PTFE, polyurethane and silicone, but many other biocompatible polymers (and/or mixtures thereof) may also be used, and therefore are included within the scope of the present invention. The present inventors have found, unexpectedly, that the use of an elastic polymer coating of this type is able to improve the fatigue resistance of the stabilizing arms (and hence of the entire intracardiac device), thereby reducing the risk of long-term breakage of the device following implantation into the heart.

Figure 23:
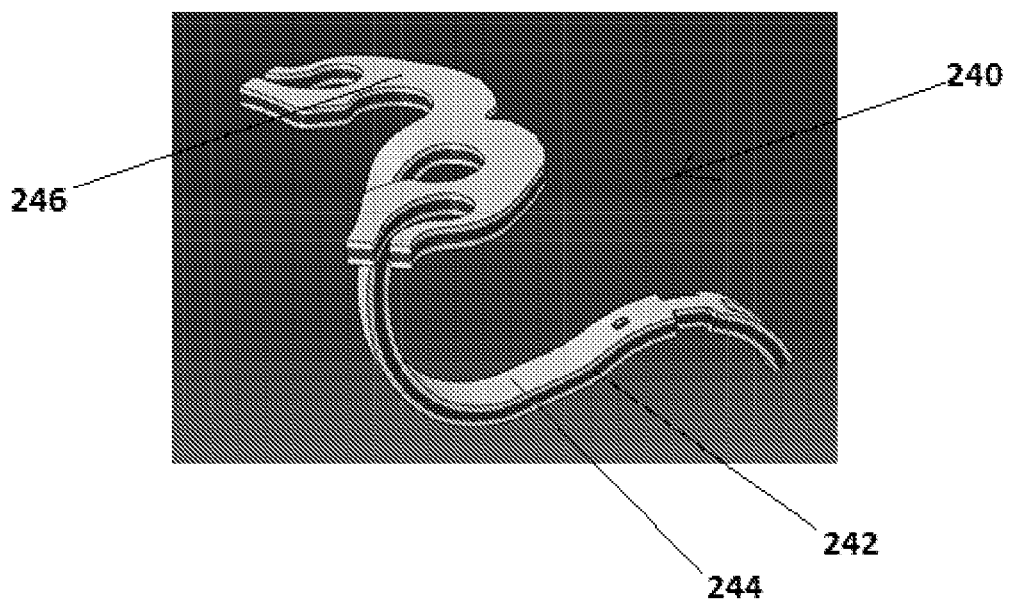
FIG. 23 depicts a further embodiment of a valve support device of the present invention, in which the stabilizing wing is coated with a layer of an elastic polymer.

An example of this embodiment of the invention is illustrated in FIG. 23, which depicts a portion of a cardiac valve support device 240, comprising a stabilizing wing 242 attached at its root (i.e. its medial end) to an annular support ring 246 (only a small portion of which is shown in this figure), wherein said stabilizing wing is coated with a layer of an elastic polymer 244.

Figure 24:
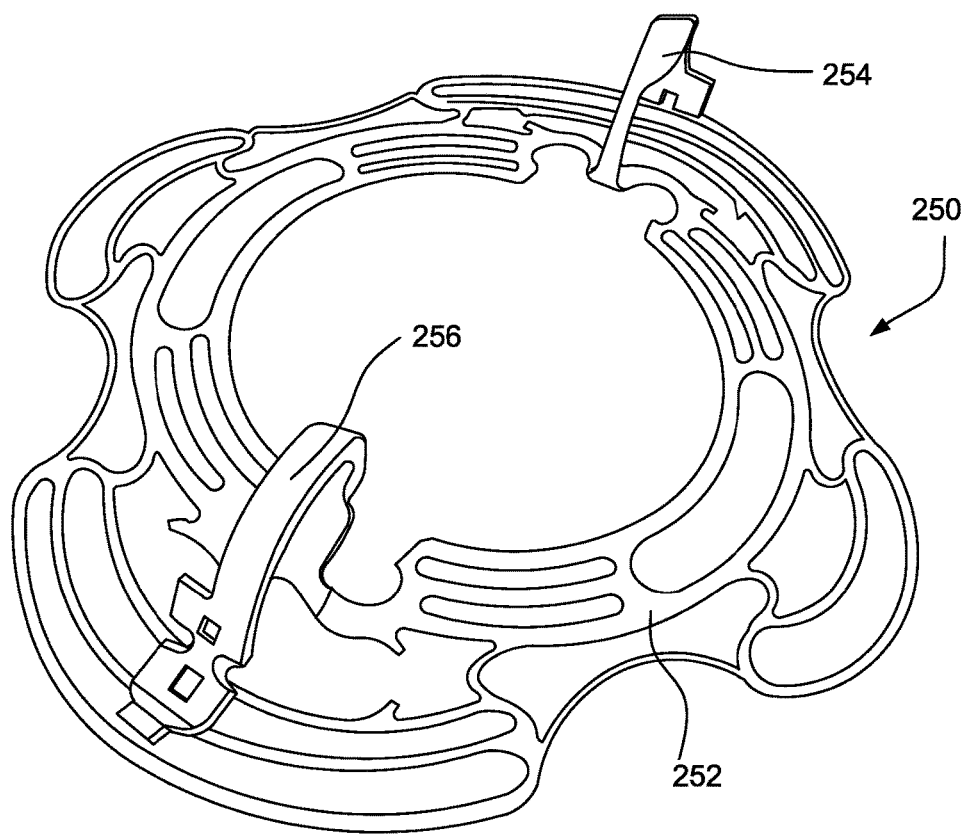
FIG. 24 shows a different view of a similar embodiment to that depicted in FIG. 23, in which the lower of the two stabilizing wings is coated with a polymeric layer.

A similar embodiment is also shown in FIG. 24, which depicts a mitral valve support device 250 comprising an annular support ring 252 and two stabilizing wings 254. It may be seen in this figure that the lower of the two wings is covered with a layer of biocompatible silicone. (It is to be noted that, generally, in this embodiment both stabilizing wings are covered by the polymeric layer; in this figure, however, the upper wing is shown uncovered, in order that the covering layer on the lower wing may be more readily seen, by means of comparing it with the uncovered wing.)

An exemplary manufacturing method for constructing this embodiment of the invention comprises the production of a sleeve or a tube of the covering material (for example, a silicone, polyurethane or PTFE tube), and pulling the tube over the attachment elements (e.g. stabilizing wings) of the device. In one preferred embodiment, the sleeve has an inner diameter of 0.2-2 mm, and surrounds the stabilizing wing in a very close-fitting manner.

In another preferred embodiment, the covering material is constructed using a "heat shrink" approach, wherein the polymeric sleeve, having a first, larger, diameter, is fitted over the attachment wings. Heat is then applied (for example with a warm air blower), thereby causing the inner diameter of the sleeve to become reduced. In this way, it is possible to 'shrink-fit' the polymeric sleeve over the stabilizing wing.

Further manufacturing methods that may be used to construct this embodiment of the device include covering the device using an electro-spinning technique, and coating said device by means of dipping the stabilizing wings in silicone, PTFE or polyurethane.

Further advantages of this last-described embodiment will now be described in the following two working examples.

Example 1

Finite Element Analysis (FEA) of the Stress-Strain Relationship in Uncovered and Silicone-Covered Stabilizing Wings The fatigue resistance of two mitral valve support devices similar to that shown in FIG. 24—one having silicone-coated stabilizing wings and one having uncovered wings—was compared using FEA (performed using Abaqus 12.1 software). Results of the metal maximal principal strain (%)

and maximal principal stress (MPa), for a wing preload of 6 mm and wing amplitude deflection of 4 mm are presented in the table below.

The analysis shows indicates that the device with the PTFE-coated wings has improved fatigue resistance, as evidenced by a reduction in both maximal principal strain (%) and maximal principal stress (MPa), as shown in the following table:

|  | With PTFE coating | Uncoated |
|---|---|---|
| Maximal principal strain (%) | 3.8 | 4.6 |
| Maximal principal stress (MPa) | 439.2 | 440.7 |

Example 2

Figure 25:
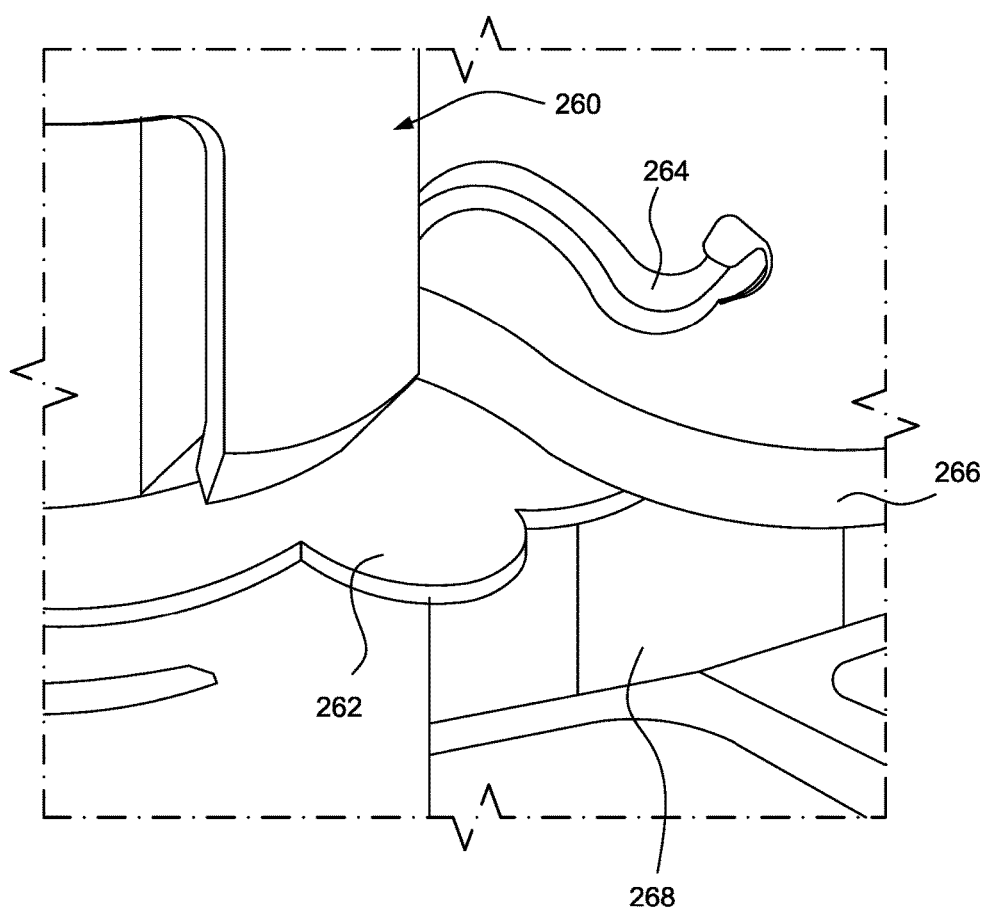
FIG. 25 is a photograph of a bench-top repetitive strain device used to compare the fatigue-resistance of valve support devices having polymer-coated stabilizing wings with those having uncoated wings.

Exemplary Fatigue Machine Testing of Valve Support Devices: Comparison of Polymer-Coated and Uncoated Stabilizing Wings A bench-top repetitive strain device 260, as shown in FIG. 25, was used to compare the fatigue-resistance of valve support devices having silicone-coated stabilizing wings with those having uncoated wings. Briefly, the body (annular ring) 262 of the support device is held within the jaws of device 260, and arranged such that one of the stabilizing wings 264 is allowed to rest on the upper surface of moveable platform 266. Then, by means of moveable piston 268 that is connected to the lower surface of said platform, the stabilizing wing is subjected to repetitive up and down movements, in order to simulate the movement of the wings during the various phases of the cardiac cycle, following implantation in the heart.

Three different designs of the valve support device were tested, and the results of the study are presented in the following table:

|  | Uncoated stabilizing wings | Silicone-coated stabilizing wings |
|---|---|---|
| Valve support device design 1 | Fracture after 3.5 million cycles | Fracture after 10.8 million cycles |
| Valve support device design 2 | Fracture after 5.8 million cycles | No fracture at 11.7 million cycles |
| Valve support device design 3 | Fracture after 13.9 million cycles | No fracture at 70 million cycles |

It may be clearly seen from these results that for each device design tested, the polymer coating resulted in each case in a more than two-fold increase in the resistance of the stabilizing wing to fracture.

Fourth Main Embodiment

This aspect of the present invention represents a departure from the stabilizing elements heretofore described. Thus, rather than providing stabilization by means of elastic forces exerted by arms or wings that are arranged such that they either rest against the heart wall or are anchored thereto, this preferred embodiment of the present invention provides mechanical stabilization elements that anchor the replacement heart valve in place by means of gripping the cardiac tissue in a controlled manner. The mechanical stabilization elements of the present invention may, in certain circumstances, represent an improvement on the previously-disclosed arms, wings and levers, since while the former permit the stabilizing forces applied to the cardiac tissues to be controlled and adjusted, the forces applied by the latter elements are uncontrolled, since they arise from the elastic nature of said elements, and are therefore essentially fixed. A further major advantage arising from the use of the mechanical stabilizing elements of this embodiment is that the absence of elastic anchoring elements results in a stabilizing mechanism that displays very little movement relative to the body of the intracardiac device (e.g. the annular ring of a mitral valve support device). Since the repetitive movement of the elastic stabilizing wings is a major cause of wing fatigue and ultimate fracture, the mechanically-stabilized devices of this aspect of the present invention are inherently much more resistant to such fatigue and breakdown.

In the case of two-ring support devices, the mechanical stabilization elements are fitted to the upper of the two rings.

This aspect of the present invention includes two main sub-embodiments, both of which generally comprise a rotatable jaw-like structure which, when in its closed position, is capable of gripping cardiac tissue (such as that of the mitral valve annulus) between its upper and lower "jaws". The two main sub-embodiments are distinguished, however, by the presence of the following specific structural elements:

Sub-embodiment 1: Spring, mechanical mechanism and internal ratchet.

Sub-embodiment 2: "Crocodile clip" fitted with a mechanical closure mechanism, either a) a worm gear activated by a torque wire (i.e. a mechanical mechanism only—no spring or ratchet elements) or b) a threaded rod that passes through a threaded hole in the clip.

Sub-Embodiment 1

Figure 26A:
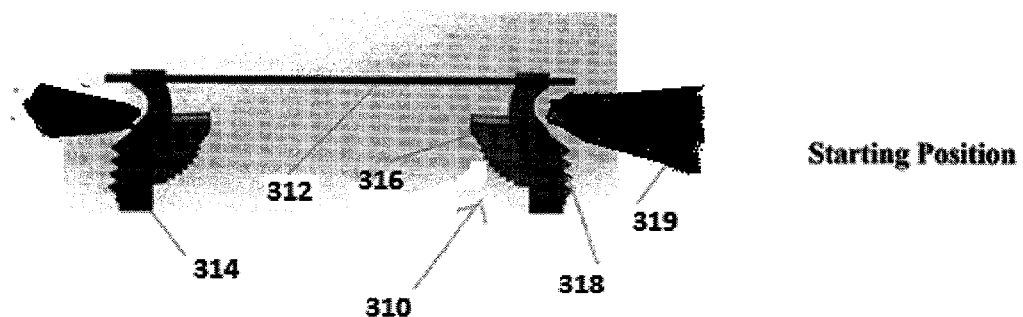
FIG. 26 depicts a further embodiment of the present invention, comprising a rotatable stabilization mechanism attached to the valve-support ring. The device is shown in its starting position, its stage 1 and stage 2 positions in FIGS. 26a, 26b and 26c, respectively.
Figure 26B:
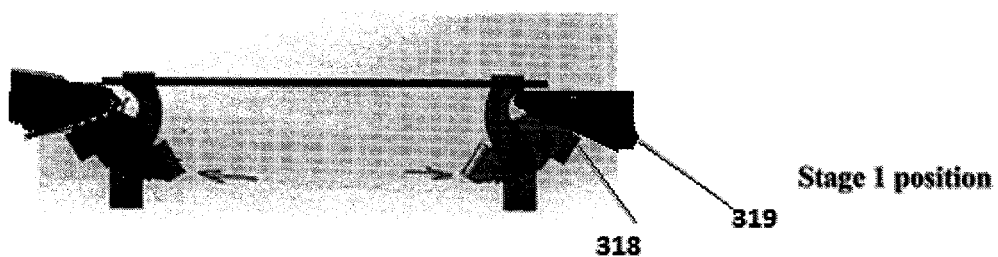

This sub-embodiment—as illustrated in FIG. 26A—comprises a rotatable stabilization mechanism 310 attached to the support ring 312 such that said mechanism is situated below the ring, wherein said mechanism comprises a fixed portion 314 attached to said ring, and a movable portion 316 that is capable of being rotated around a horizontal axis (at right angles to the longitudinal axis of the valve support), wherein said movable portion has a ridged gripping surface 318, such that when said mechanism is caused to rotate around its axis (as shown in FIG. 26B), said ridged gripping surface is caused to face upwards, towards the ring support, such that the distance between the lateral end of said gripping surface and the lower surface of the ring is reduced when said mechanism is rotated.

Figure 26C:
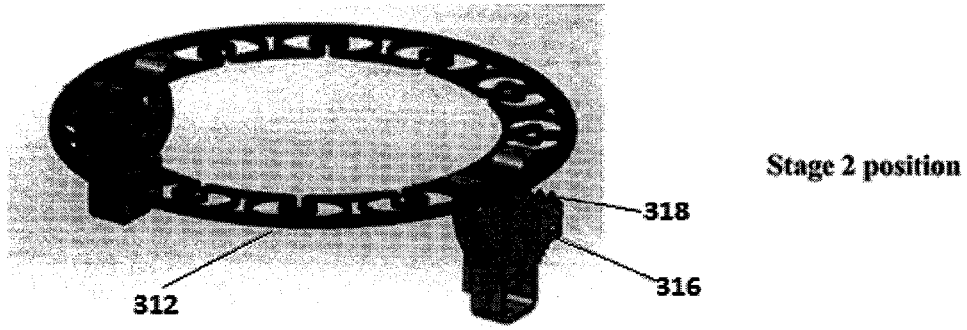

The rotatable mechanism has essentially three different positions, as illustrated in FIG. 26:

A. Starting position: The ring support is implanted such that the support ring 312 is above the level of the annular tissue 319, and the ridged gripping surface 318 of the mechanism is facing away from said annular tissue.

B. Stage 1 position: The rotatable mechanism is activated (by a control wire or other mechanism) such that the ridged gripping surface 318 is brought into contact with the surface of the annular tissue 319.

C. Stage 2 position: Following implantation of the replacement heart valve within the central space of the valve support, lateral expansion of said valve causes further rotation of the movable portion 316 of the mechanism, such that the distance between the ridged gripping surface thereof (318) and the lower surface of support ring 312 is reduced, thereby increasing the gripping force exerted by the mechanism on the annular tissue.

In addition to the fixed and movable portions described above, the rotatable mechanism further comprises an internal coiled spring and a ratchet mechanism.

The purpose of the spring element is to apply a force on the rotatable mechanism such that it moves from the starting position to the stage 1 position. This is done by activating a release mechanism (for example a control wire) that permits the spring to close elastically towards its resting position. The spring is physically connected to the rotatable mechanism, such that when the spring jumps towards its closed, resting position, it takes the movable portion of the mechanism with it. The rest position of the spring is designed such that when attained, it causes the gripping surface of the movable portion to come to rest on the inferior surface of the annular tissue. When the movable portion is caused to further rotate (by means of radially-outward forces exerted by the expanding replacement valve) to its stage 2 position, the spring moves (together with the movable portion of the rotatable mechanism) by plastic deformation, since it has exceeded its elastic range of movement.

The purpose of the ratchet mechanism is to prevent accidental reverse rotation of the rotatable mechanism, thereby inadvertently causing release of the gripped annular tissue by the device. The device also comprises a release mechanism for releasing the ratchet mechanism thereby permitting controlled reverse rotation, in the event that it is necessary to intentionally release grip on the tissue.

Figure 27:
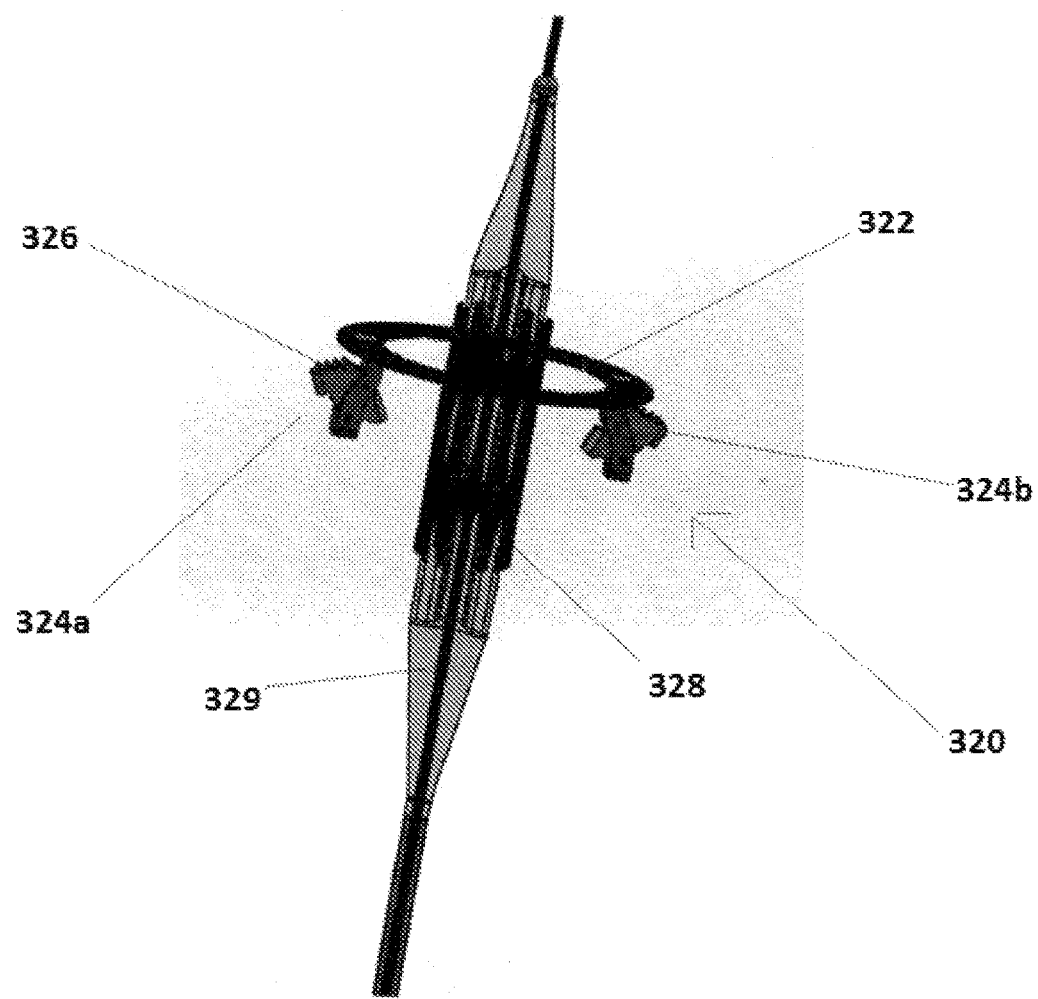
FIG. 27 depicts the same embodiment of the mitral valve support device as shown in FIG. 26 in its stage 1 position, i.e. prior to expansion and deployment of the replacement cardiac valve.

FIG. 27 depicts a mitral valve support of the present invention 320 in its stage 1 position, said device comprising a support ring 322 on to which is fitted two rotatable stabilization mechanisms 324a and 324b, located in a position which is essentially opposite each other along the circumference of said support ring. The location of the stabilizing mechanisms corresponds with the position of the mitral valve commissures. The scope of this invention includes more than two such stabilizing mechanisms, and two mechanisms in different locations on the device, with a preferred embodiment in which the mechanisms are essentially opposite each other, in accordance with the locations of the commissures of the mitral valve. It will be noted that the ridged gripping surface 326 of the movable portion of the mechanism is facing in a generally upwards direction, but is not yet completed aligned along the horizontal plane. At this stage of the valve implantation procedure, the mitral valve support 320 has already been implanted into its working position at the mitral valve annulus (not shown), while a stented replacement valve 328 and its associated balloon expansion device 329 are in their collapsed, delivery conformations.

Figure 28:
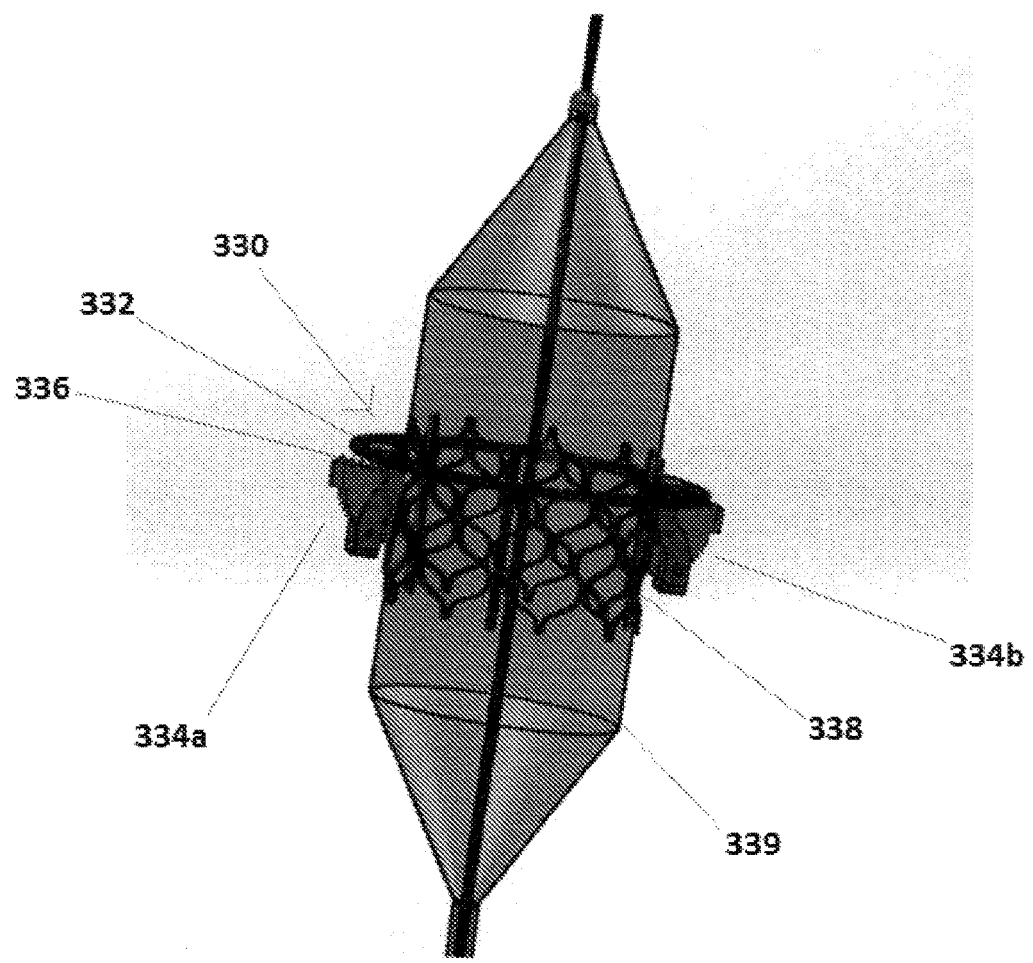
FIG. 28 shows the same mitral valve support device as in FIG. 27, but in its stage 2 position, i.e. following expansion and deployment of the replacement valve.

FIG. 28 shows the same mitral valve support device 330 that was depicted in FIG. 27, following expansion of the stented replacement valve 338, by means of expansion of balloon 339, i.e. in its stage 2 position. The radially-outward forces exerted by the expanding replacement valve 338 have caused the movable portion of the rotatable stabilization mechanisms 334a and 334b to undergo further rotation (when compared with the stage 1 position of FIG. 27), such that the ridged gripping surface 336 of said movable portion is now disposed horizontally, is essentially parallel with the horizontal plane of support ring 332.

Figure 29:
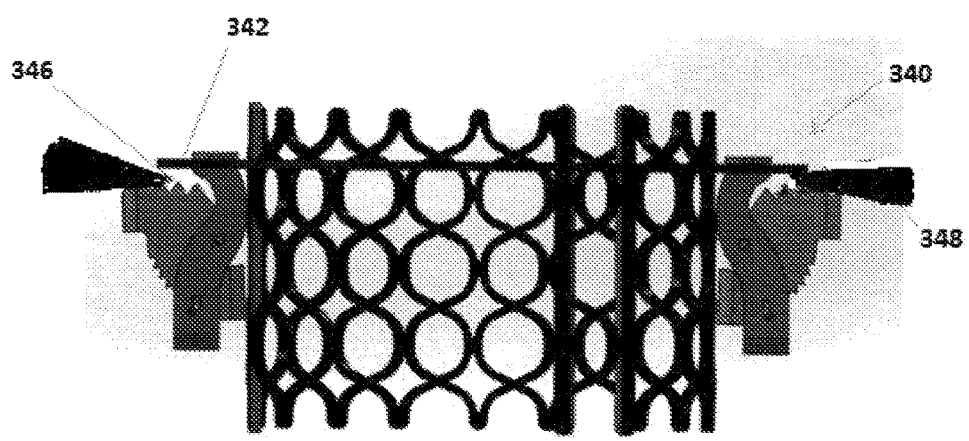
FIG. 29 depicts the same device as in FIG. 28 (i.e. in its stage 2 position) in side view, and illustrates the manner in which the cardiac tissue is gripped between the ridged gripping surface of the mechanical stabilization means and the mitral valve support ring.

The in situ stage 2 position of the mitral valve support device 340 is shown in side view in FIG. 29. It may be seen from this view that the annular tissue 348 is now firmly gripped between the ridged gripping surface 346 of the movable portion of the rotatable stabilization mechanism, and the lower surface of mitral valve support ring 342.

Sub-Embodiment 2

Figure 30:
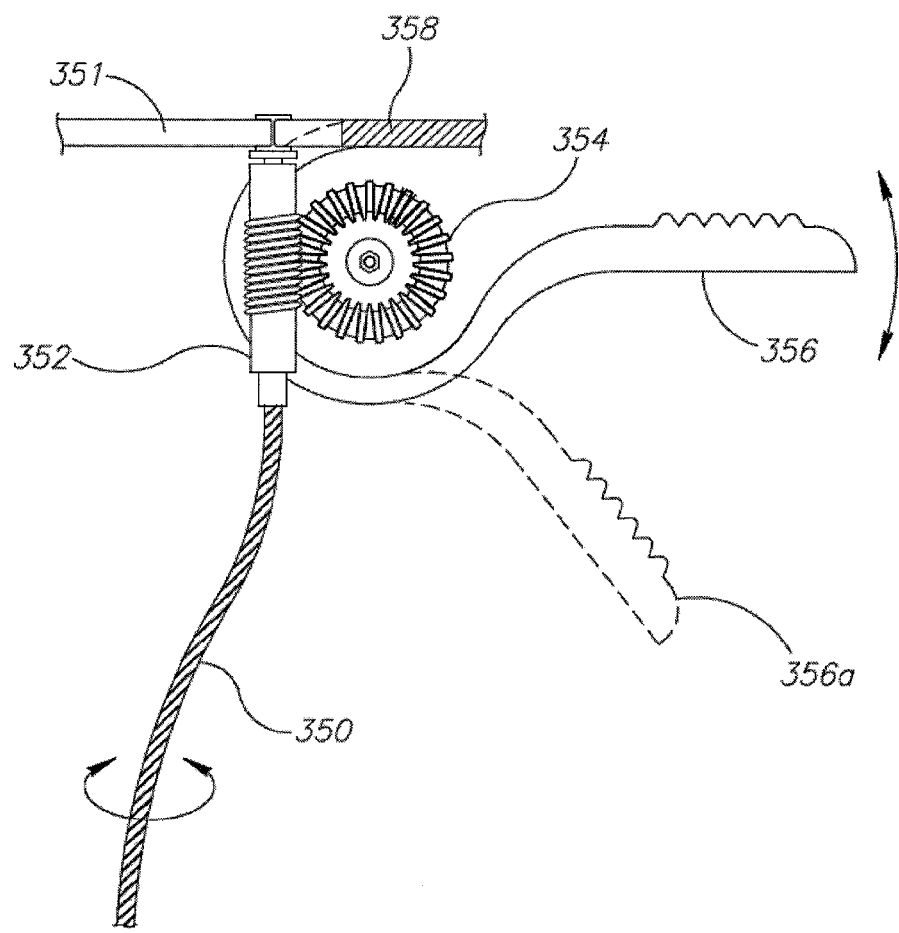
FIG. 30 illustrates another preferred embodiment of the invention, in which a worm gear actuated by a torque wire is used to deploy and control the mechanical stabilization means.

This sub-embodiment comprises a purely mechanical mechanism comprising a movable arm fitted with a ridged gripping surface, which is pivotally movable in relation to a fixed arm that is attached to a cardiac device, for example a mitral valve support ring (or a transcatheter prosthetic mitral valve). The combination of these two arms is capable of functioning as a jaw mechanism, in order to grip the valve annulus therein. While many different arrangements are possible, two preferred mechanisms for causing movement of the movable arm in relation to the fixed arm are:

a) Worm gear actuated by a torque wire (as shown in side view in FIG. 30)

FIG. 30 illustrates this embodiment of the invention, in which the fixed arm 358 of the rotatable stabilization mechanism is attached to the valve support ring 351. In this implementation, rotation of the torque wire 350 causes corresponding rotation of worm 352, which in turn causes worm gear 354 to rotate. Since said worm gear is attached to movable arm 356, said movable arm is thereby caused to open or close in relation to fixed arm 358, depending on the direction in which said torque wire is rotated. The movable arm is shown in both its fully closed position 356 and its fully open position 356a. When in its fully closed position in situ, the tissue of the mitral annulus (not shown) is trapped between the ridged upper surface of movable arm 356 and the lower, ridged surface of fixed arm 358.

Figure 31:
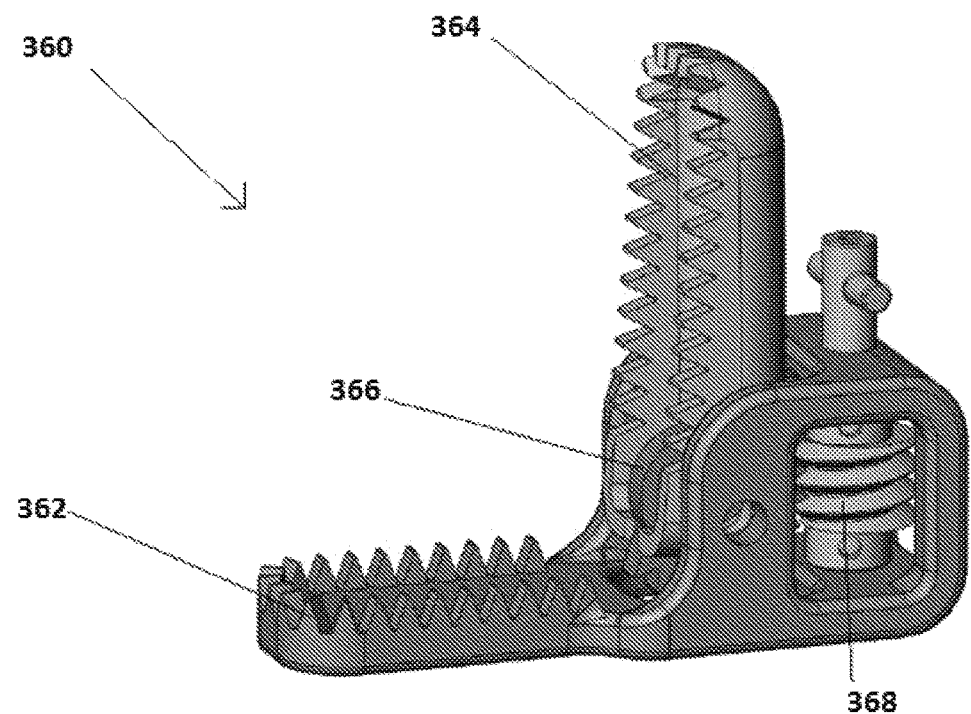
FIG. 31 provides a close-up perspective view of the embodiment of FIG. 30, with the rotatable stabilization mechanism in its fully-open position.

FIG. 31 provides a close-up perspective view of the implementation shown in FIG. 30, wherein the rotatable stabilization mechanism 360 is in its fully-open position. As shown, the jaw mechanism of this implantation comprises a fixed arm 362 and a movable arm 364, wherein the latter element is aligned vertically, i.e. essentially along the longitudinal axis of the ring support (not shown) to which stabilization mechanism 360 is attached. The inner surfaces of both the fixed and movable arms are ridged, in order to improve the ability of the stabilization mechanism to grip the annular tissue. This figure also shows worm gear 366, with some of its teeth engaging with the screw thread of worm 368.

Figure 32:
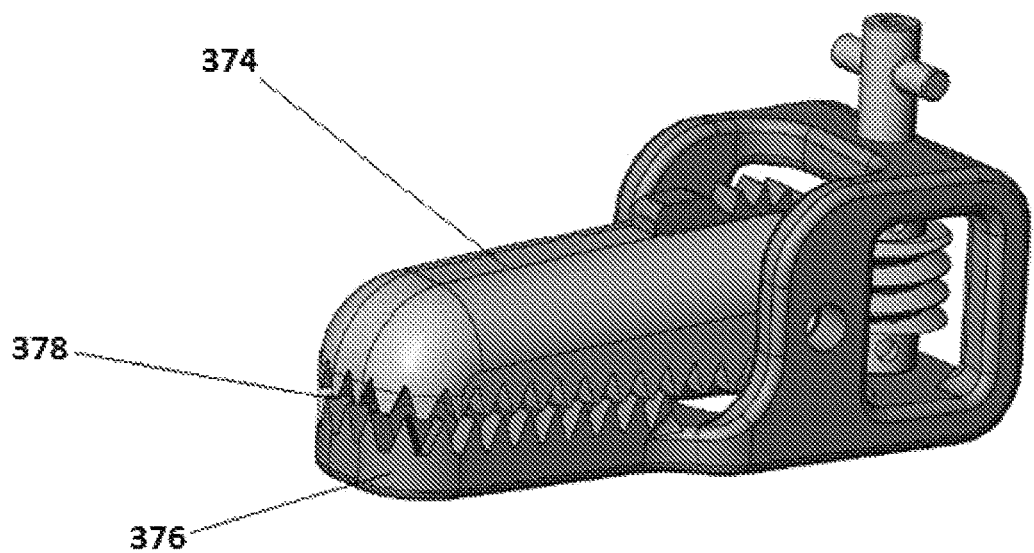
FIG. 32 illustrates the same embodiment as shown in FIG. 31, but in its fully-closed position.
Figure 33:
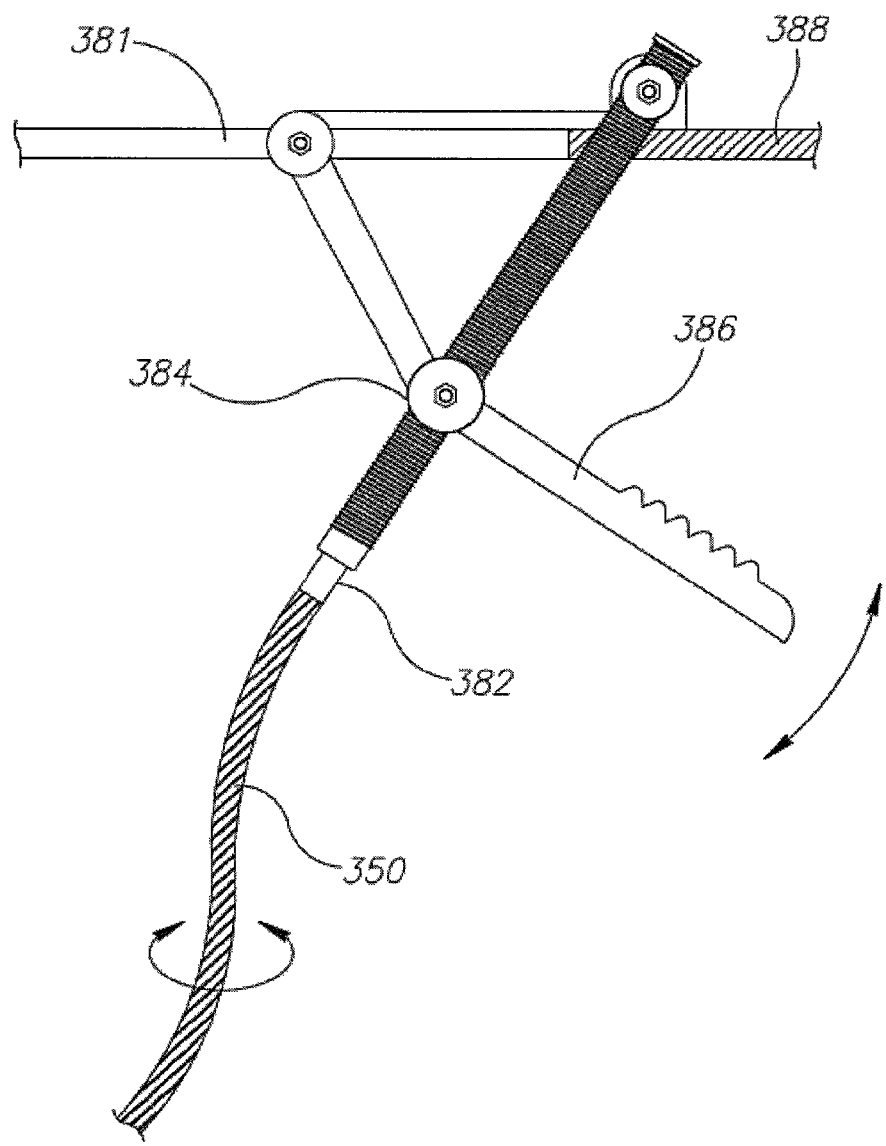
FIG. 33 depicts an alternative embodiment of the present invention in which the mechanical stabilization mechanism is controlled by means of a threaded rod passing through a threaded aperture in the movable arm.

FIG. 32 presents a close-up perspective view of the same device shown in FIG. 31, but in its fully-closed position, with movable arm 374 disposed horizontally. Following implantation of the valve support device into its working position at the mitral valve annulus, said movable arm 374 is closed onto fixed arm 376, such that the tissue of said mitral valve annulus becomes firmly held in the space 378 between the inner ridged surfaces of said movable and fixed arms.

b) Threaded rod passing through a threaded aperture in the movable arm (as shown in side view in FIG. 33).

FIG. 33 illustrates this implementation, in which rotation of a torque wire 380 connected to threaded rod 382 causes corresponding rotation of said threaded rod through threaded aperture 384 that pierces movable arm 386. In this way, the rotatory movement of torque wire 380 is translated into movement of the movable arm 386 along threaded rod 382, leading to opening or closing of said movable arm in relation to fixed arm 388, in accordance with the direction in which said torque wire is rotated. As shown in FIG. 33, fixed arm 388 is attached to valve support ring 381.

The cardiac support ring of the present invention described hereinabove and illustrated in the accompanying figures is generally constructed from medical-grade Nitinol sheet, preferably having a thickness between 0.25 and 1.2 mm. Other biocompatible metals having the desired shape-memory properties may also be used in place of Nitinol. Following layout of the intended design on the metal sheet, laser cutting is used to cut out said design. Subsequently, the final product is formed using heat treatment and mandrels, as is well known to skilled artisans in the field. Final processing stages may optionally include oxide layer removal by means of sandblasting and electropolishing.

The various embodiments of the rotatable stabilization mechanism of this aspect of the present invention may be manufactured from Nitinol, Cobalt base alloy, Stainless steel etc., by techniques that are well-known to the skilled artisan in the field, including laser cutting, stamping, die forming, cold forming, EDM wire cutting, CNC bending. The rotatable stabilization mechanisms may be attached to the valve support ring by means of techniques such as laser welding, soldering, electrical spot welding, fastener insertion and mechanical assembly.

Typically, the outer diameter of the support element of the support ring of the presently-disclosed device will be in the range of 23-60 mm, while its inner diameter will have a value in the range of 23-35 mm. Devices having diameters smaller or larger than the limits of these ranges may also be required in certain circumstances, and are included within the scope of the present invention.

Additionally, as previously explained, the device of the invention may be a prosthetic valve (for example a transcatheter prosthetic mitral valve which may be balloon expandable or self-expandable), which is to be placed in the annulus and anchored in place by the anchoring element of the invention.

The delivery and implantation of the devices illustrated and described herein may be achieved by endovascular and transapical methods, as described in detail in many publications including WO2013/128436 and WO2012/031141. The device of the invention is described herein mainly in the context of the mitral valve of the left ventricle. However, this is intended as a non-limiting example, and the device may similarly be used in the position of the tricuspid valve, between the right atrium and right ventricle, or in other positions such as the aortic or pulmonary valve positions.

The invention claimed is:

1. An intracardiac device suitable for minimally-invasive delivery, wherein said device comprises a device body and one or more stabilizing elements attached to said device body, wherein said stabilizing elements are selected from the group consisting of:
   a) stabilizing wings having at least one portion with a thickness greater than that of the device body;
   b) stabilizing wings comprising one or more primary anchoring arms, which are capable of applying upwards axially-directed stabilizing forces, and one or more support arms;
   c) stabilizing wings having a metal wire coil wound therearound;
   d) stabilizing wings having a leaf spring attached thereto;
   e) polymer-coated stabilizing wings; and
   f) mechanical stabilization elements comprising a rotatable jaw-like structure, wherein said device comprises one or more mechanical stabilization elements, each of said elements comprising a jaw-like structure, wherein said jaw-like structure comprises a fixed arm and a movable arm, said movable arm being pivotable in relation to said fixed arm around a common pivot point, and wherein said mechanism further comprises mechanical rotation means for causing said movable arm to rotate around said pivot point, thereby causing either closure or opening of said jaw-like structure.

2. The intracardiac device according to claim 1, wherein the mechanical rotation means comprises a spring which is biased such that it causes closure of the jaw-like structure, a release mechanism for said spring and a ratchet mechanism for preventing accidental reverse rotation of said jaw-like structure.

3. The intracardiac device according to claim 2, wherein the spring release mechanism comprises a control wire.

4. The intracardiac device according to claim 1, wherein the mechanical rotation means comprises a worm gear actuated by a torque wire.

5. The intracardiac device according to claim 1, wherein the mechanical rotation means comprises a threaded rod passing through a threaded aperture that pierces the movable arm.

6. The intracardiac device according to claim 1, wherein said device is selected from the group consisting of single-ring valve support device, two-ring valve support device and prosthetic cardiac valve.

7. The intracardiac device according to claim 6, wherein said device is a single-ring valve support device suitable for minimally-invasive implantation within the mitral valve annulus.

\* \* \* \* \*